United States Patent
Gluckman et al.

(10) Patent No.: US 8,637,567 B2
(45) Date of Patent: Jan. 28, 2014

(54) COGNITIVE ENHANCEMENT AND COGNITIVE THERAPY USING GLYCYL-L-2-METHYLPROLYL-L-GLUTAMIC ACID

(75) Inventors: Peter David Gluckman, Auckland (NZ); Jian Guan, Auckland (NZ); Mary-Anne Woodnorth, Auckland (NZ); Margaret Anne Brimble, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 356 days.

(21) Appl. No.: 12/903,844

(22) Filed: Oct. 13, 2010

(65) Prior Publication Data
US 2011/0112033 A1    May 12, 2011

Related U.S. Application Data

(63) Continuation of application No. 11/315,784, filed on Dec. 21, 2005, now abandoned, which is a continuation-in-part of application No. 10/155,864, filed on May 24, 2002, now Pat. No. 7,041,314.

(60) Provisional application No. 60/293,853, filed on May 24, 2001.

(51) Int. Cl.
*A61K 9/00* (2006.01)
*A61K 31/499* (2006.01)

(52) U.S. Cl.
USPC ........ 514/423; 514/10.8; 514/15.1; 514/17.9; 514/18.2; 514/237.8; 514/249; 514/289; 514/291; 514/312; 514/365; 514/414; 514/8.4; 514/8.6; 514/8.8; 424/451; 424/464; 424/85.2; 424/131.1; 424/85.5

(58) Field of Classification Search
USPC .......... 514/423, 10.8, 15.1, 17.9, 18.2, 237.8, 514/249, 289, 291, 312, 365, 414, 8.4, 8.6, 514/8.8, 8.9; 424/451, 464, 85.2, 131.1, 424/85.5
See application file for complete search history.

(56) References Cited

FOREIGN PATENT DOCUMENTS

WO    WO99/65509    * 12/1999

OTHER PUBLICATIONS

Barilli et al, Mechanisms of Aging and Development, 1998, vol. 106, pp. 57-92.*

* cited by examiner

*Primary Examiner* — Savitha Rao
(74) *Attorney, Agent, or Firm* — D. Benjamin Borson; Borson Law Group, PC

(57) ABSTRACT

This invention provides compounds, compositions and methods for treating a cognitive disorder or memory disorder in animals that result from aging or other neurodegenerative condition. In particular, compounds of this invention can stimulate neural cell growth, increased amounts of cells containing a key enzyme needed for production of the cholinergic neurotransmitter, and can improve memory and cognitive function in animals who have experienced a loss of memory or cognitive function.

16 Claims, 24 Drawing Sheets
(2 of 24 Drawing Sheet(s) Filed in Color)

---

I. MODIFY GLYCINE RESIDUE

G*PE

II. MODIFY GLUTAMIC ACID RESIDUE i. α-carboxylic acid residue
ii. γ-carboxylic acid residue
iii. GPE diesters

GPE*

III. MODIFY PEPTIDE LINKAGES i. modify Pro - α-methylproline
ii. modify Glu - *N*-Methylglutamic acid
         α-Methylglutamic acid GP*E and GPE#

I. MODIFY GLYCINE RESIDUE

G*PE

II. MODIFY GLUTAMIC ACID RESIDUE

GPE* i. α-carboxylic acid residue
ii. γ-carboxylic acid residue
iii. GPE diesters

III. MODIFY PEPTIDE LINKAGES

GP*E and GPE# i. modify Pro - α-methylproline
ii. modify Glu - N-Methylglutamic acid
    α-Methylglutamic acid

COGNITIVE ENHANCEMENT AND COGNITIVE THERAPY USING GLYCYL-L-2-METHYLPROLYL-L-GLUTAMIC ACID

CLAIM OF PRIORITY

This application is a continuation of U.S. patent application Ser. No. 11/315,784, filed Dec. 21, 2005 now abandoned, which is a continuation in part of U.S. patent application Ser. No. 10/155,864, filed May 24, 2002, now U.S. Pat. No. 7,041,314, which claims the priority under 35 U.S.C. 119(e) to U.S. Provisional Application No. 60/293,853, filed May 24, 2001. This application also claims priority, through U.S. patent application Ser. No. 11/315,784, to United States Utility patent application Ser. No. 11/314,424 filed Dec. 20, 2005, entitled: "Effects of G-2Methyl-Prolyl-Glutamate On Neurodegeneration," Inventors: Peter D. Gluckman, Greg Brian Thomas, Jim Guan, Mike Dragunow, Ashmit Kumar Anand, Nicole Kerlero de Rosbo and Frank Sieg, now U.S. Pat. No. 7,605,177. Each of the above applications and patents is expressly incorporated herein fully by reference.

BACKGROUND

1. Field of the Invention

This invention relates to synthetic analogs and peptidomimetics of glycyl-L-prolyl-L-glutamic acid (GPE). In particular, this invention relates to GPE analogs and peptidomimetics that are anti-apoptotic and anti-necrotic, to methods of making them, to pharmaceutical compositions containing them, and to their use to enhance cognitive function and/or treat memory disorders in animals.

2. Description of Related Art

EP 0 366 638 discloses GPE (a tri-peptide consisting of the amino acids Gly-Pro-Glu) and its di-peptide derivatives Gly-Pro and Pro-Glu. EP 0 366 638 discloses that GPE is effective as a neuromodulator and is able to affect the electrical properties of neurons.

WO95/172904 discloses that GPE has neuroprotective properties and that administration of GPE can reduce damage to the central nervous system (CNS) by the prevention or inhibition of neuronal and glial cell death.

WO 98/14202 discloses that administration of GPE can increase the effective amount of choline acetyltransferase (ChAT), glutamic acid decarboxylase (GAD), and nitric oxide synthase (NOS) in the central nervous system (CNS).

WO99/65509 discloses that increasing the effective amount of GPE in the CNS, such as by administration of GPE, can increase the effective amount of tyrosine hydroxylase (TH) in the CNS to increase TH-mediated dopamine production in the treatment of diseases such as Parkinson's disease.

WO02/16408 discloses GPE analogs capable of inducing a physiological effect equivalent to GPE within a patient. The applications of the GPE analogs include the treatment of acute brain injury and neurodegenerative diseases, including but not limited to, injury or disease in the CNS.

The disclosures of these and other documents referred to in this application (including in the Figures of those documents) are explicitly incorporated herein fully by reference as if each one was individually incorporated by reference.

SUMMARY

In its first aspect, this invention provides compounds of Formula 1 and Formula 2: where:

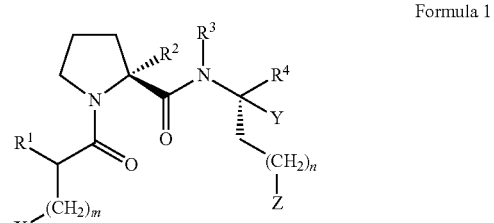

Formula 1

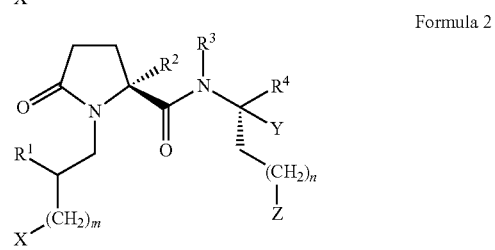

Formula 2 m is 0 or 1;
n is 0 or 1;
X is H or —$NR^6R^7$;
Y is H, alkyl, —$CO_2R^5$, or —$CONR^6R^7$;
Z is H, alkyl, —$CO_2R^5$ or —$CONR^6R^7$;
$R^1$ is H, alkyl, or aralkyl;
$R^2$, $R^3$, and $R^4$ are independently H or alkyl;
each $R^5$ is independently H, alkyl, or a fatty alcohol residue;
each $R^6$ and $R^7$ is independently H, alkyl, or aralkyl, or
—$NR^6R^7$ is pyrrolidino, piperidino, or morpholino;
or a lactone formed when a compound where Y is —$CO_2$(alkyl) and Z is —$CO_2H$ or where Y is —$CO_2H$ and Z is —$CO_2$(alkyl) is lactonized;
and the pharmaceutically acceptable salts thereof,
provided that the compound is not GPE, N-Me-GPE, GPE amide, APE, GPQ or a salt thereof.

Another aspect the invention provides methods for treatment of an animal having a condition characterized by memory disorder, comprising administration of an effective amount of Glycyl-L-2-Methylpropyl-L-Glutamic Acid (G-2MePE) to the animal, optionally in conjunction with at least one other therapeutic agent for the treatment of the memory loss or impairment.

Another aspect the invention provides methods of enhancing cognitive function in an animal that can benefit from such enhancement, comprising administration of an effective amount of G-2MePE to the animal, optionally in conjunction with at least one other cognitive function enhancing agents.

In yet another aspect, this invention provides pharmaceutical compositions comprising a pharmaceutically acceptable excipient and a therapeutically effective amount of at least one compound of this invention. These compositions find use as anti-apoptotic agents, anti-necrotic agents, cognitive function enhancing agents, and therapeutics useful in treatment of memory disorders, and for conditions where administration of a GPE analog or peptidomimetic is indicated.

In another aspect, this invention provides methods of treating an animal having a disease or injury capable of treatment by administration of a GPE analog or peptidomimetic, comprising administration to that animal of at least one compound of this invention, optionally in conjunction with at least one other therapeutic agent for the disease being treated.

In a further aspect, this invention provides methods of preparing the compounds of the first aspect of this invention.

BRIEF DESCRIPTION OF THE DRAWINGS

This invention is described with reference to specific embodiments thereof. Other aspects and features of this invention can be understood with reference to the Figures, in which:

FIG. 12 depicts a graph showing effects of GPE on cortical neurons injured with okadaic acid.

FIG. 13 depicts a graph showing effects of G-2MePE on cortical neurons injured with okadaic acid.

FIG. 14 depicts a graph showing effects of G-2MePE, GPE on cerebellar microexplants injured with okadaic acid.

FIG. 15 depicts a graph showing effects of G-2MePE or GPE on striatal cells injured with okadaic acid.

FIG. 18A shows the maze acquisition profiles across days for the different groups. FIG. 18B shows the proportion of correct maze choices averaged across days for the groups.

DETAILED DESCRIPTION

Definitions

Figure 1:
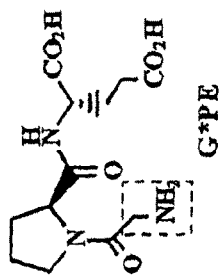
FIG. 1 is a general scheme for preparation of synthetic analogues of GPE of the invention.
Figure 1:
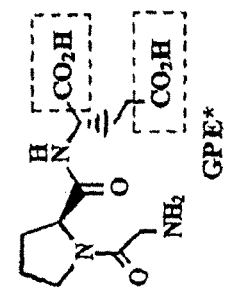
Figure 1:
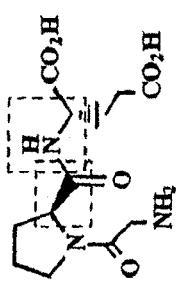

The term "about" with reference to a dosage or time refers to a particular variable and a range around that variable that is within normal measurement error or is within about 20% of the value of the variable.

The term "alkyl" means a linear saturated hydrocarbyl group having from one to six carbon atoms, or a branched or cyclic saturated hydrocarbyl group having from three to six carbon atoms. Exemplary alkyl groups include straight and branched chain, or cyclic alkyl groups, methyl, ethyl, isopropyl, cyclopropyl, tert-butyl, cyclopropylmethyl, and hexyl.

The term "animal" includes humans and non-human animals, such as domestic animals (cats, dogs, and the like) and farm animals (cattle, horses, sheep, goats, swine, and the like).

The term "aralkyl" means a group of the formula —$(CH_2)_{1-2}$Ar, where Ar is a 5- or 6-membered carbocyclic or heterocyclic aromatic ring, optionally substituted with 1 to 3 substituents selected from Cl, Br, —OH, —O-alkyl, —$CO_2R^8$ (where $R^8$ is H or alkyl), or —$NR^8R^9$, where $R^8$ is as described previously and $R^9$ is H or alkyl. Exemplary aralkyl groups include benzyl, 2-chlorobenzyl, 4-(dimethylamino)benzyl, phenethyl, 1-pyrrolylmethyl, 2-thienylmethyl, and 3-pyridylmethyl.

The term "disease" includes any unhealthy condition of an animal including particularly Parkinson's disease, Huntington's disease, Alzheimer's disease, multiple sclerosis, diabetes, motor disorders, seizures, and cognitive dysfunctions due to aging.

The term "fatty alcohol residue" is a linear hydrocarbyl group having from seven to twenty carbon atoms, optionally containing up to three carbon-carbon double bonds. Exemplary fatty alcohol residues include decyl, pentadecyl, hexadecyl (cetyl), octadecyl (stearyl), oleyl, linoleyl, and eicosyl.

The term "growth factor" means an extracellular polypeptide-signaling molecule that stimulates a cell to grow or proliferate.

The term "injury" includes any acute damage of an animal including non-hemorrhagic stroke, traumatic brain injury, perinatal asphyxia associated with fetal distress such as that following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, cerebral trauma and toxic injury.

"Memory disorders" or "cognitive disorders" are disorders characterized by permanent or temporary impairment or loss of ability to learn, memorize or recall information. Memory disorder can result from normal aging, injury to the brain, tumors, neurodegenerative disease, vascular conditions, genetic conditions (Huntington's disease), hydrocephalus, other diseases (Pick's disease, Creutzfeld-Jakob disease, AIDS, meningitis), toxic substances, nutritional deficiency, biochemical disorders, psychological or psychiatric dysfunctions. The presence of memory disorder in a human can be established thorough examination of patient history, physical examination, laboratory tests, imagining tests and neuropsychological tests. Standard neuropsychological tests include but are not limited to Brief Visual Memory Test-Revised (BVMT-R), Cambridge Neuropsychological Test Automated Battery (CANTAB), Children's Memory Scale (CMS), Contextual Memory. Test, Continuous Recognition Memory Test (CMRT), Controlled Oral Word Association Test and Memory Functioning Questionnaire, Denman Neuropsychology Memory Scale, Digit Span and Letter Number Sequence sub-test of the Wechsler Adult Intelligence Scale-III, Fuld Object Memory Evaluation (FOME), Graham-Kendall Memory for Designs Test, Guild Memory Test, Hopkins Verbal Learning Test, Learning and Memory Battery (LAMB), Memory Assessment Clinic Self-Rating Scale (MAC-S), Memory Assessment Scales (MAS), Randt Memory Test, Recognition memory Test (RMT), Rey Auditory and Verbal Learning Test (RAVLT), Rivermead Behavioural Memory Test, Russell's Version of the Wechsler Memory Scale (RWMS), Spatial Working Memory, Test of Memory and Learning (TOMAL), Vermont Memory Scale (VMS), Wechsler Memory Scale, Wide Range Assessment of Memory and Learning (WRAML).

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The term "pharmaceutically acceptable salt" means a salt that is pharmaceutically acceptable and has the desired pharmacological properties. Such salts include salts that can be formed where acidic protons present in the compounds react with inorganic or organic bases. Suitable inorganic salts include those formed with the alkali metals, e.g. sodium and potassium, magnesium, calcium, and aluminium. Suitable organic salts include those formed with organic bases such as amines e.g. ethanolamine, diethanolamine, triethanolamine, tromethamine, N-methylglucamine, and the like. Salts also include acid addition salts formed by reaction of an amine group or groups present in the compound with an acid. Suitable acids include inorganic acids (e.g. hydrochloric and hydrobromic acids) and organic acids (e.g. acetic acid, citric acid, maleic acid, and alkane- and arene-sulfonic acids such as methanesulfonic acid and benzenesulfonic acid). When there are two acidic groups present in a compound, a pharmaceutically acceptable salt may be a mono-acid mono-salt or a di-salt; and similarly where there are more than two acidic groups present, some or all of such groups can be salified. The same reasoning can be applied when two or more amine groups are present in a compound.

The term "protecting group" is a group that selectively blocks one or more reactive sites in a multifunctional compound such that a chemical reaction can be carried out selectively on another unprotected reactive site and such that the group can readily be removed after the selective reaction is complete.

The term "therapeutically effective amount" means the amount of an agent that, when administered to an animal for treating a disease, is sufficient to effect treatment for that disease as measured using a test system recognized in the art.

The term "treating" or "treatment" of a disease may include preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "functional deficit" means a behavioral deficit associated with neurological damage. Such deficits include deficits of gait, as observed in patients with Parkinson's disease, motor abnormalities as observed in patients with Huntington's disease. Functional deficit also includes abnormal foot placement and memory disorders described herein.

The term "seizure" means an abnormal pattern of neural activity in the brain that results in a motor deficit or lack of motor control resulting in abnormal motion, including spasmodic motion. "Seizure" includes electroencephalographic abnormalities, whether or not accompanied by abnormal motor activity.

Implicit hydrogen atoms (such as hydrogen atoms on a pyrrolidine ring, etc.) are omitted from the formulae for clarity, but should be understood to be present.

Compounds of the Invention

While the broadest definition of the invention is set out in the Summary, certain compounds of this invention are presently described.

Some compounds of this invention are compounds where:
(a) the compounds are compounds of Formula 1;
(b) m is 0;
(c) n is 1;
(d) at least one of X, Y, $R^1$, $R^2$, $R^3$, $R^4$, and $R^5$ is not hydrogen;
(e) X is —$NR^6R^7$; and
(f) Y is —$CO_2R^5$ or —$CO_2NR^6R^7$; and
(g) Z is —$CO_2R^5$ or —$CO_2NR^6R^7$.

Other compounds of the invention are compounds of Formula 1 wherein X is —$NR^6R^7$ and $R^6$ and $R^7$ are independently alkyl or aralkyl. The more preferred embodiment is a compound of Formula I wherein X is —$NR^6R^7$ and both $R^6$ and $R^7$ are alkyl.

Yet another compound of the invention is G-2MePE, a compound of Formula 1 wherein m is 0, n is 1, R1=R3=R4=H, R2 is methyl, X is $NR^6R^7$ where $R^6$=$R^7$=H, Y is $CO_2R^5$ where $R^5$=H, Z is $CO_2R^5$ where $R^5$=H.

Pharmacology and Utility

Compounds of this invention can have anti-apoptotic, anti-necrotic and neuroprotective effects. Their activity in vivo can be measured by cell counts, specific staining of desired markers, or by methods such as those discussed in Klempt N D et al: Hypoxia-ischemia induces transforming growth factor β1 mRNA in the infant rat brain. Molecular Brain Research: 13: 93-101. Their activity can also be measured in vitro using methods known in the art or described herein.

Conditions affecting the brain function become prevalent in aging populations. Memory loss and memory impairment are distressing to patients affected and their families. Memory loss or impairment can result from normal aging, injury to the brain, neurodegenerative disease and psychological or psychiatric dysfunctions. It is therefore of great benefit to patients, their families and to society that novel compounds are identified and characterized that enhance memory and/or cognitive function, and treat or prevent memory loss or impairment.

It is desirable to study effects of potential therapeutic agents in animal systems. One such useful system is the rat. It is known that with aging, rats and other animals (including human beings) can exhibit symptoms of memory loss, memory impairment and other cognitive dysfunctions. Further, it is known that studies in rats of therapeutic agents are predictive of therapeutic effects in humans. Thus, studies of effects of GPE and G-2MePE and cognitive function in aging rats are reasonably predictive of therapeutic effects of those agents in aging human beings that have or are prone to acquiring memory deficits or other cognitive dysfunction. Compounds of this invention can enhance cognitive function and/or treat memory disorders. The cognitive enhancing activity and therapeutic activity in vivo can be measured by standard neuropsychological or behavioural tests known to individuals skilled in the art. Such tests can be chosen from a wide range of available tests described above, and will vary depending on the cognitive function to be tested and the condition of the animal.

Standard behavioral tests useful for testing cognitive function in experimental animals include but are not limited to the Morris Water Maze test, passive avoidance response test, object recognition test, the 8-arm radial maze test and the T-maze test. These tests are directly applicable to studies of effects of GPE and G-2MePE on cognitive function in aging rats.

The compounds of this invention are also expected to have pharmacological and therapeutic activities similar to those of GPE, and these activities may be measured by the methods known in the art, and discussed in the documents cited herein, and by methods used for measuring the activity of GPE.

The therapeutic ratio of a compound can be determined, for example, by comparing the dose that gives effective anti-apoptotic and anti-necrotic activity in a suitable in vivo model such as a hypoxic-ischemic injury (Sirimanne E S, Guan J, Williams C E and Gluckman P D: Two models for determining the mechanisms of damage and repair after hypoxic-ischemic injury in the developing rat brain. Journal of Neuroscience Methods: 55: 7-14, 1994) in a suitable animal species such as the rat, with the dose that gives significant observable side-effects in the test animal species.

The therapeutic ratio of a compound can also be determined, for example by comparing the dose that gives effective cognitive function enhancement or treats a memory disorder in a suitable in vivo model (Examples 4, 5 and 6 below) in a suitable animal species such as the rat, with the dose that gives significant weight loss (or other observable side-effects) in the test animal species.

Pharmaceutical Compositions and Administration

In general, compounds of this invention can be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease or injury, the severity of the disease, the age and relative health of the animal being treated, the potency of the compound(s), and other factors. As anti-apoptotic, anti-necrotic, anti-neurodegenerative, therapeutically effective amounts of compounds of this invention can range from about 0.001 milligrams per kilogram (mg/kg) to about 100 (mg/kg) mass of the animal, for example, about 0.1 to about 10 mg/kg, with lower doses such as about 0.001 to about 0.1 mg/Kg, e.g. about 0.01 mg/Kg, being appropriate for administration through the cerebrospinal fluid, such as by intracerebroventricular administration, and higher doses such as about 1 to about 100 mg/Kg, e.g. about 10 mg/Kg, being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

In general, compounds of this invention can be administered as pharmaceutical compositions by one of the following routes: oral, topical, systemic (e.g. transdermal, intranasal, or by suppository), or parenteral (e.g. intramuscular, subcutaneous, or intravenous injection), by administration to the CNS (e.g. by intraspinal or intercisternal injection); by implantation, and by infusion through such devices as osmotic pumps, implantable pumps, transdermal patches, and the like. Compositions can take the form of tablets, pills, capsules, semi-solids, powders, sustained release formulation, solutions, suspensions, elixirs, aerosols, or any other appropriate compositions; and comprise at least one compound of this invention in combination with at least one pharmaceutically acceptable or physiological acceptable excipient. Suitable excipients are well known to persons of ordinary skill in the art, and they, and the methods of formulating the compositions, may be found in such standard references as Gennaro A R: Remington: The Science and Practice of Pharmacy, $20^{th}$ ed., Lippincott, Williams & Wilkins, 2000. Suitable liquid carriers, especially for injectable solutions, include water, aqueous saline solution, aqueous dextrose solution, glycols, and the like, with isotonic solutions being preferred for intravenous, intraspinal, and intracisternal administration and vehicles such as artificial cerebrospinal fluid being also especially suitable for administration of the compound to the CNS. The above text is expressly incorporated herein fully by reference.

Compounds of this invention can be administered after or before onset of a condition that is likely to result in neurodegeneration or a symptom thereof. For example, it is known that hypoxia/ischemia can occur during coronary artery bypass graft (CABG) surgery. Thus, a patient can be pre-treated with a compound of this invention before being placed on an extracorporeal oxygenation system. In some embodiments, it can be desirable to administer a compound of this invention beginning about 4 hours before surgery or before an event that is likely to lead to traumatic or other neurological injury. In other embodiments, it can be desirable to infuse a compound of this invention during the surgery or during a surgical procedure to repair a neurological injury. Compounds of this invention can also be used in emergency situations, for example in a patient that has just experienced a stroke, hypoxic event, traumatic brain injury or other acute insult. In such situations, a compound of this invention can be administered immediately after a diagnosis of neural injury is made.

In some situations, kits containing compound of this invention can be prepared in advance of use in the field. A kit can contain a vial containing a compound of the invention in a pharmaceutically acceptable formulation (e.g., for injection), along with a syringe or other delivery device, and instructions for use. In situations in which a seizure is diagnosed, a compound of this invention can be administered along with an anticonvulsant. Many anticonvulsants are known in the art and need not be described in detail herein.

Additionally, "secondary" neurological injuries can occur after a primary insult such as a traumatic injury, stroke or surgical procedure. For example, after a stroke, penetrating brain injury or a CABG procedure, inflammation of neural tissue can lead to neurodegeneration. Secondary injuries can be reflected by increased activation of inflammatory cells (e.g., astrocytes and/or microglia), and actions of inflammatory mediators can cause neurological damage. Thus, in some embodiments, it can be desirable to administer a compound of this invention for periods beginning before the insult, to up to about 100 hours after the insult. In other embodiments, it can be desirable to administer a compound of this invention beginning before the insult, during the insult and after the insult, either continuously, as an infusion, or in discrete doses separated by a desired time interval.

Compounds of this invention can also be suitably administered by a sustained-release system. Suitable examples of sustained-release compositions include semi-permeable polymer matrices in the form of shaped articles, e.g., films, or microcapsules. Sustained-release matrices, include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981), ethylene vinyl acetate (Langer et al., supra), or poly-D-(-)-3-hydroxybutyric acid (EP 133,988). Sustained-release compositions also include a liposomally entrapped compound. Liposomes containing the compound are prepared by methods known per se: DE 3,218,121; Epstein et al., 1985; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102, 324. Ordinarily, liposomes are of the small (from or about 200 to 800 Angstroms) unilamellar type in which the lipid content is greater than about 30 mole percent cholesterol, the selected proportion being adjusted for the most efficacious therapy. Each and every of the above-identified publications is expressly herein incorporated fully by reference, as if each had been separately so incorporated.

Compounds of this invention can also be attached to polyethylene glycol ("PEGylated") to increase their lifetime in vivo, based on, e.g., the conjugate technology described in WO 95/32003.

Desirably, if possible, when administered as an anti-apoptotic agent, an anti-necrotic agent, or an anti-neurodegenerative agent, compounds of this invention can be administered orally. The amount of a compound of this invention in the composition can vary widely depending on the type of composition, size of a unit dosage, kind of excipients, and other factors well known to those of ordinary skill in the art. In general, the final composition can comprise from about 0.0001 percent by weight (% w) to about 10% w of the compound of this invention, preferably about 0.001% w to about 1% w, with the remainder being a excipient or excipients.

A composition may optionally contain, in addition to a compound of this invention, at least one agent selected from, for example, growth factors and associated derivatives (insulin-like growth factor-I (IGF-I), insulin-like growth factor-II (IGF-II), transforming growth factor-$\beta$1, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine (MK-801), selegiline; glutamate antagonists such as, NPS1506, GV1505260, MK-801, GV150526; AMPA antagonists such as 2,3-dihydroxy-6-nitro-7-sulfamoylbenzo (f)quinoxaline (NBQX), LY303070 and LY300164; anti-inflammatory agents directed against the addressin MAd-CAM-1 and/or its integrin $\alpha$4 receptors ($\alpha$4$\beta$1 and $\alpha$4$\beta$7), such as anti-MAdCAM-1 mAb MECA-367 (ATCC accession no. HB-9478). Most of these agents, especially the peptides such as the growth factors, etc. are not orally active, and will require administration by injection or infusion.

Preparation of Compositions

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic $\alpha$-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. Reaction of N-(alkoxymethyl)dialkylamines and N,N'-methylenebisdialkylamines with isocyanides. Chem. Pharm. Bull.: 23(1), 219-221, 1975. Each of the above-identified publications is herein expressly incorporated fully by reference as though individually so incorporated.

Starting materials, intermediates, and compounds of this invention may be isolated and purified using conventional techniques, including filtration, distillation, crystallization, chromatography, and the like. They may be characterized using conventional methods, including physical constants and spectral data.

Compounds of this invention may be prepared by the methods described below and as given in the Examples.

Compounds of Formula 1 are analogues of GPE, or modifications thereof, such as esters or amides. In general, they may be prepared by methods such as are already well-known to persons of ordinary skill in the art of peptide and modified peptide synthesis, following the reaction schemes set forth in the FIGS. 1-11 accompanying this specification, or by following other methods well-known to those of ordinary skill in the art of the synthesis of peptides and analogs.

Conveniently, synthetic production of the polypeptides of the invention may be according to the solid-phase synthetic method described by Merrifield et al. Solid phase peptide synthesis. I. The synthesis of a tetrapeptide: J. Amer. Chem. Soc.: 85, 2149-2156, 1963. This technique is well understood and is a common method for preparation of peptides. The general concept of this method depends on attachment of the first amino acid of the chain to a solid polymer by a covalent bond. Succeeding protected amino acids are added, on at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_2$), and phenylmethoxycarbonyl (Z or CBZ). Additional protective groups are identified in Merrifield, cited above, as well as in McOmie JFW: Protective Groups in Organic Chemistry, Plenum Press, New York, 1973, both references expressly incorporated fully herein.

General procedures for preparing peptides of this invention involve initially attaching a carboxyl-terminal protected amino acid to the resin. After attachment the resin is filtered, washed and the protecting group (desirably BOC) on the I-amino group of the carboxyl-terminal amino acid is removed. The removal of this protecting group must take place, of course, without breaking the bond between that amino acid and the resin. The next amino, and if necessary, side chain protected amino acid, is then coupled to the free I-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, Peptide Synthesis, 2nd ed, John Wiley and Sons, New York, 1976. For example, the peptides of the invention may also be synthesized using standard solution peptide synthesis methodologies, involving either stepwise or block coupling of amino acids or peptide fragments using chemical or enzymatic methods of amide bond formation. (See, e.g. H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.) These solution synthesis methods are well known in the art. Each of the above-identified publications is expressly incorporated herein fully by reference as though individually so incorporated.

Commercial peptide synthesizers, such as the Applied Biosystems Model 430A, are available for the practice of these methods.

A person of ordinary skill in the art will not have to undertake undue experimentation, taking account of that skill and the knowledge available, and of this disclosure, in developing one or more suitable synthetic methods for compounds of this invention.

Figure 2:
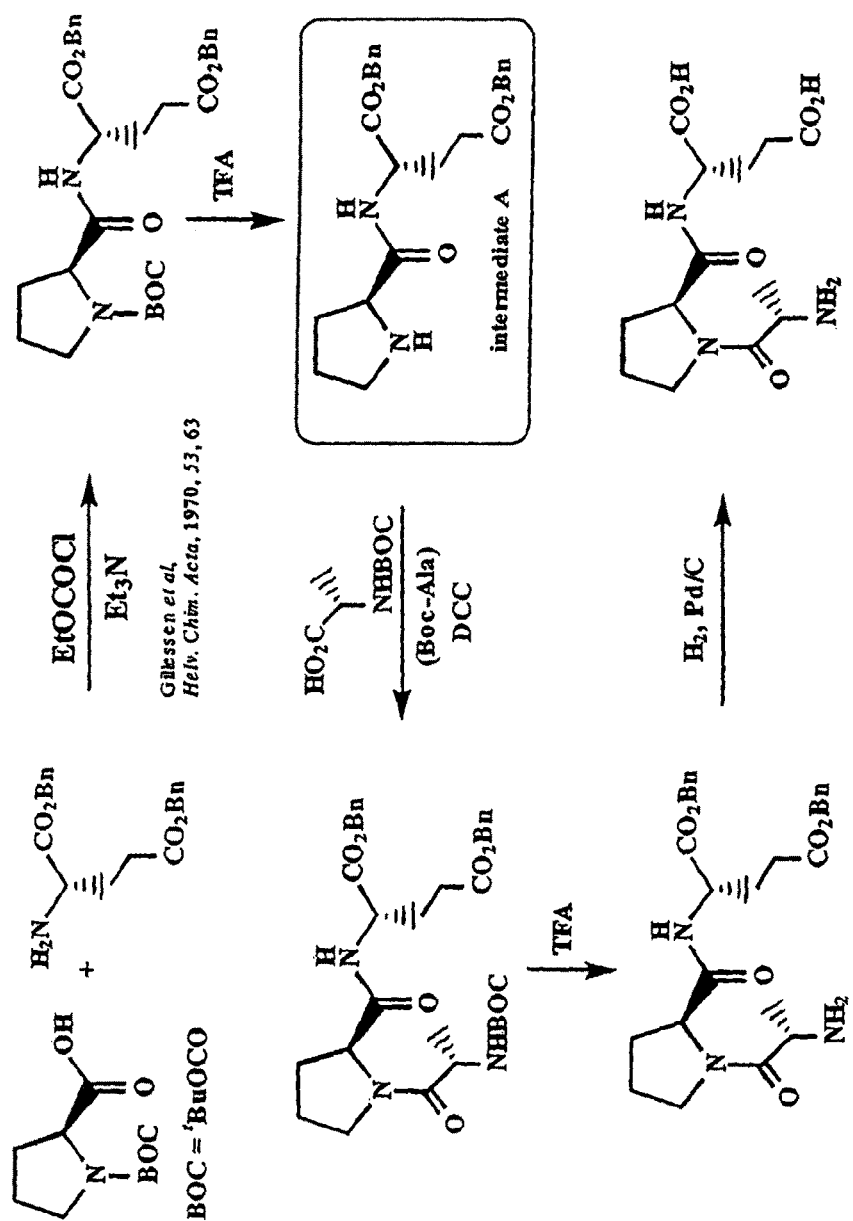
FIGS. 2 and 3 depict schemes for modifying glycine residues on GPE.
Figure 3:
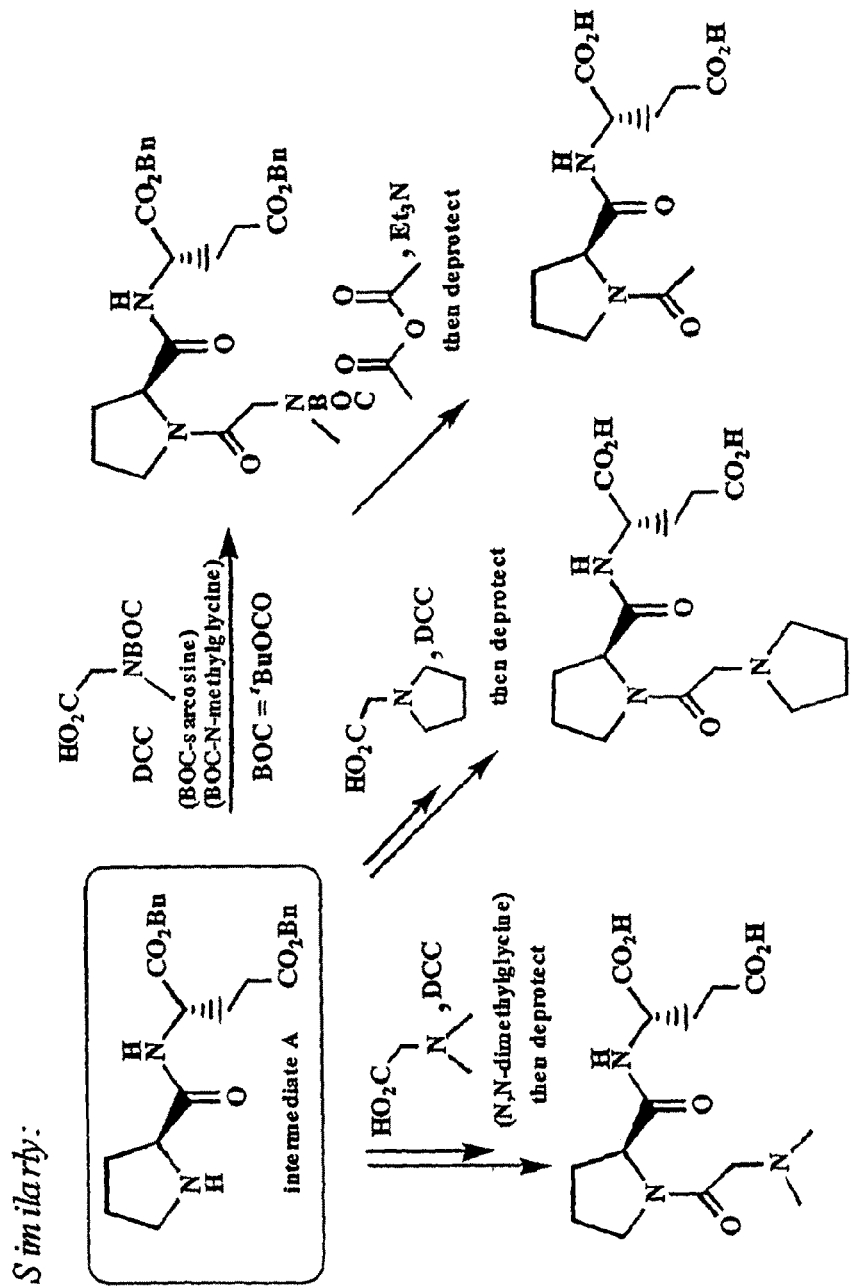
Figure 4:
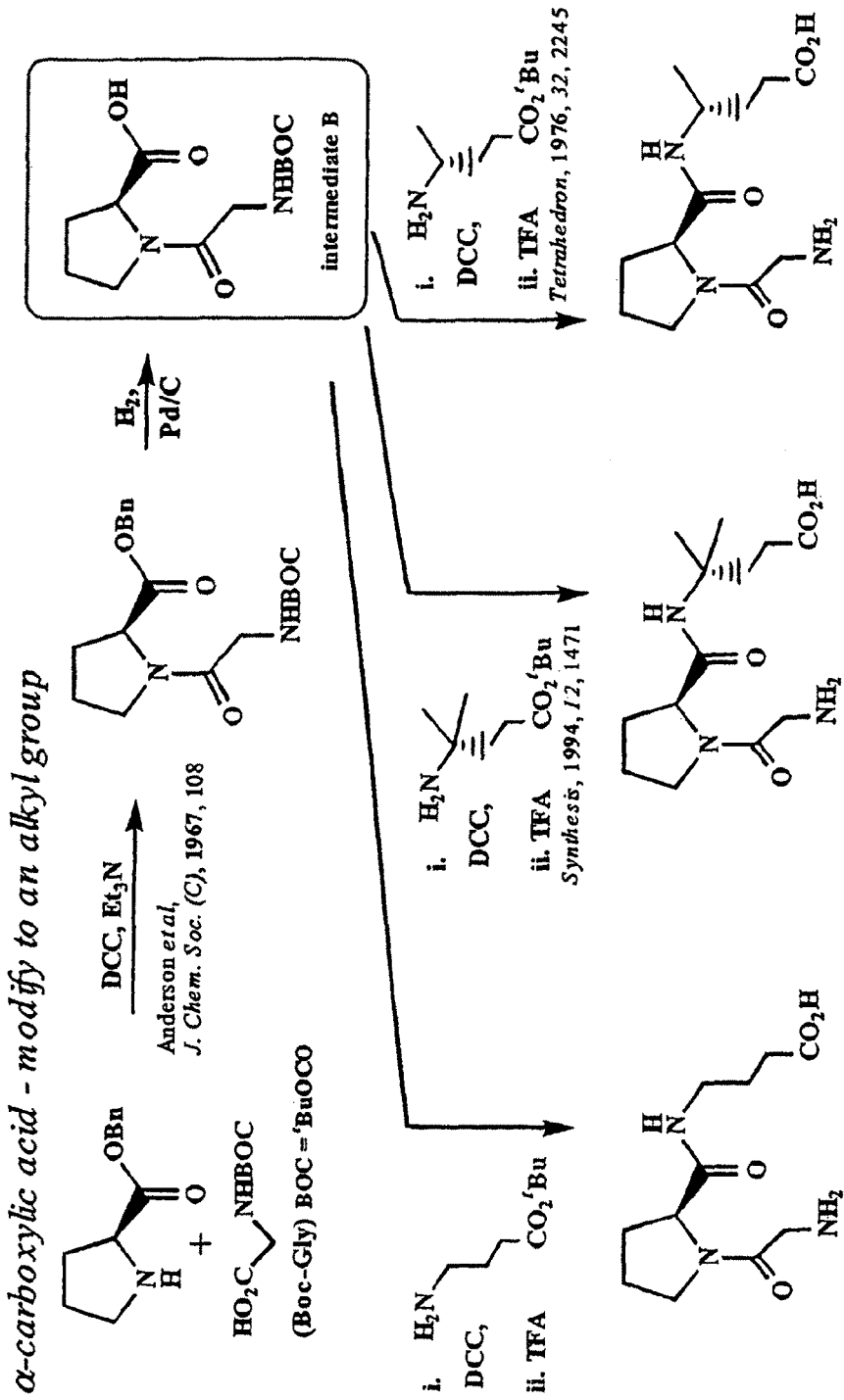
FIGS. 4 through 9 depict schemes for modifying glutamic acid residues of GPE.
Figure 5:
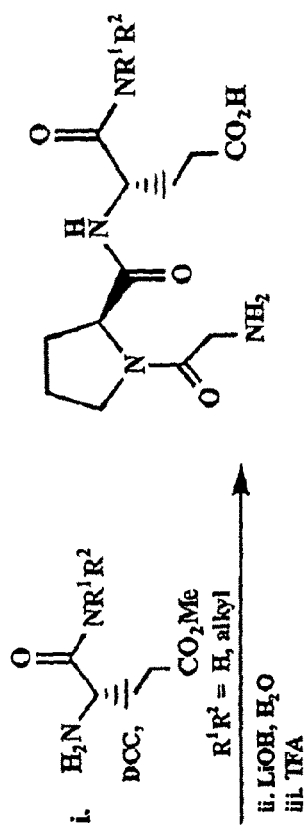
Figure 5:
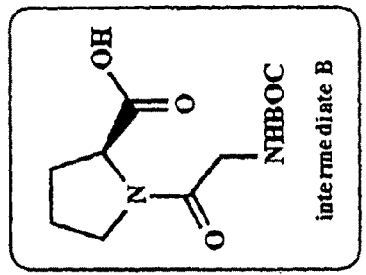
Figure 5:
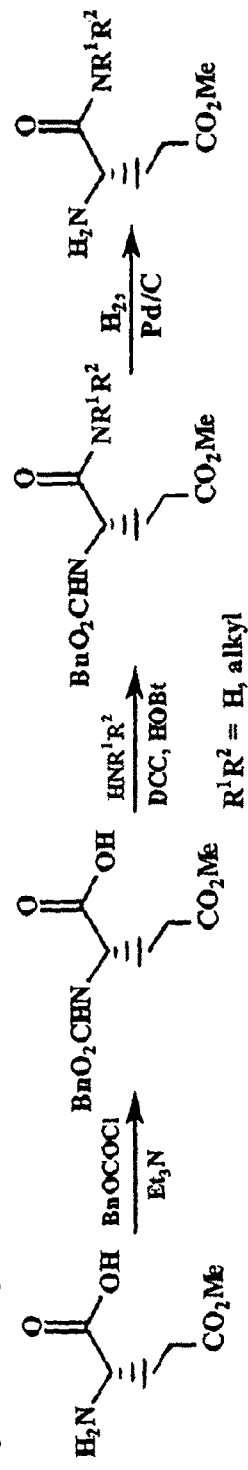
Figure 6:
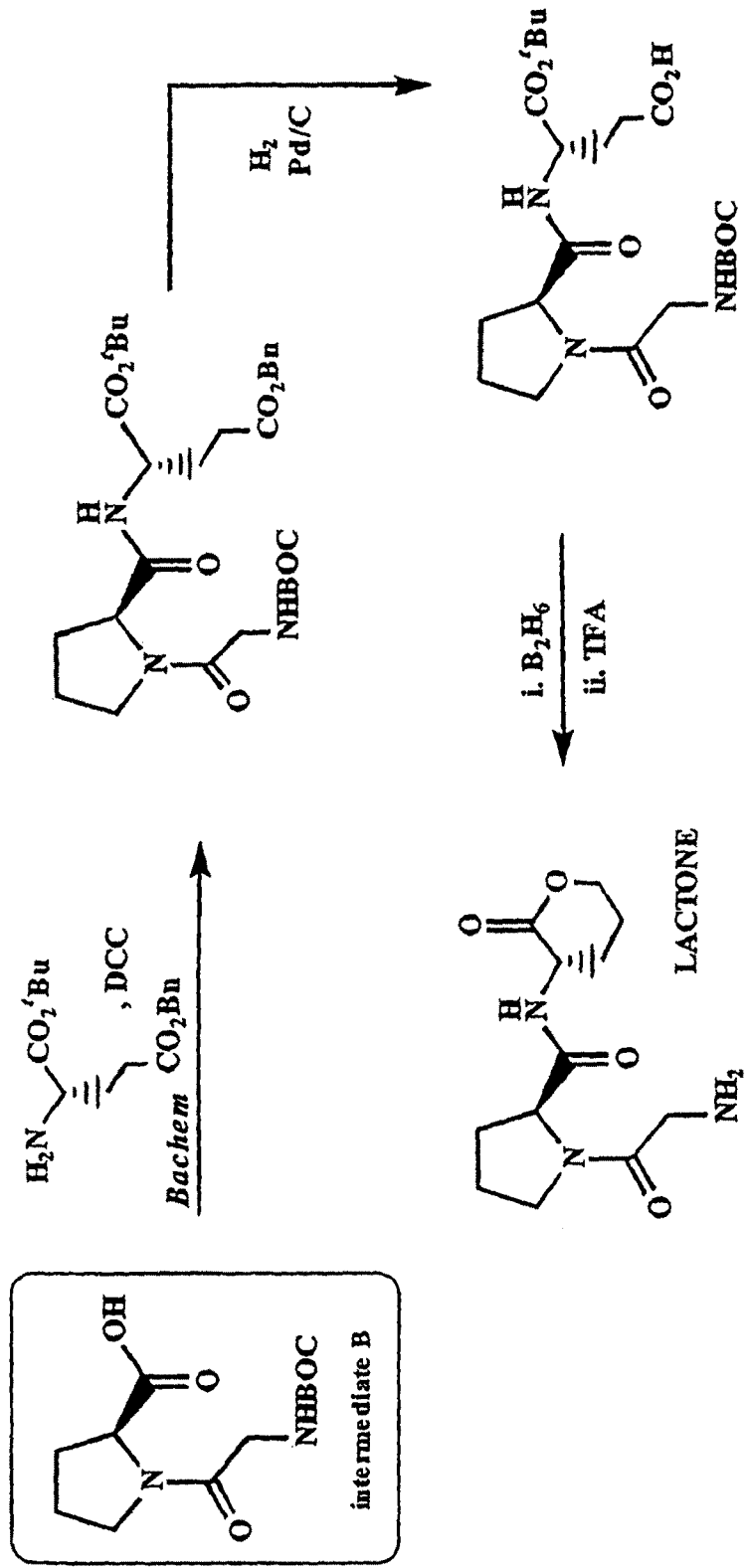
Figure 7:
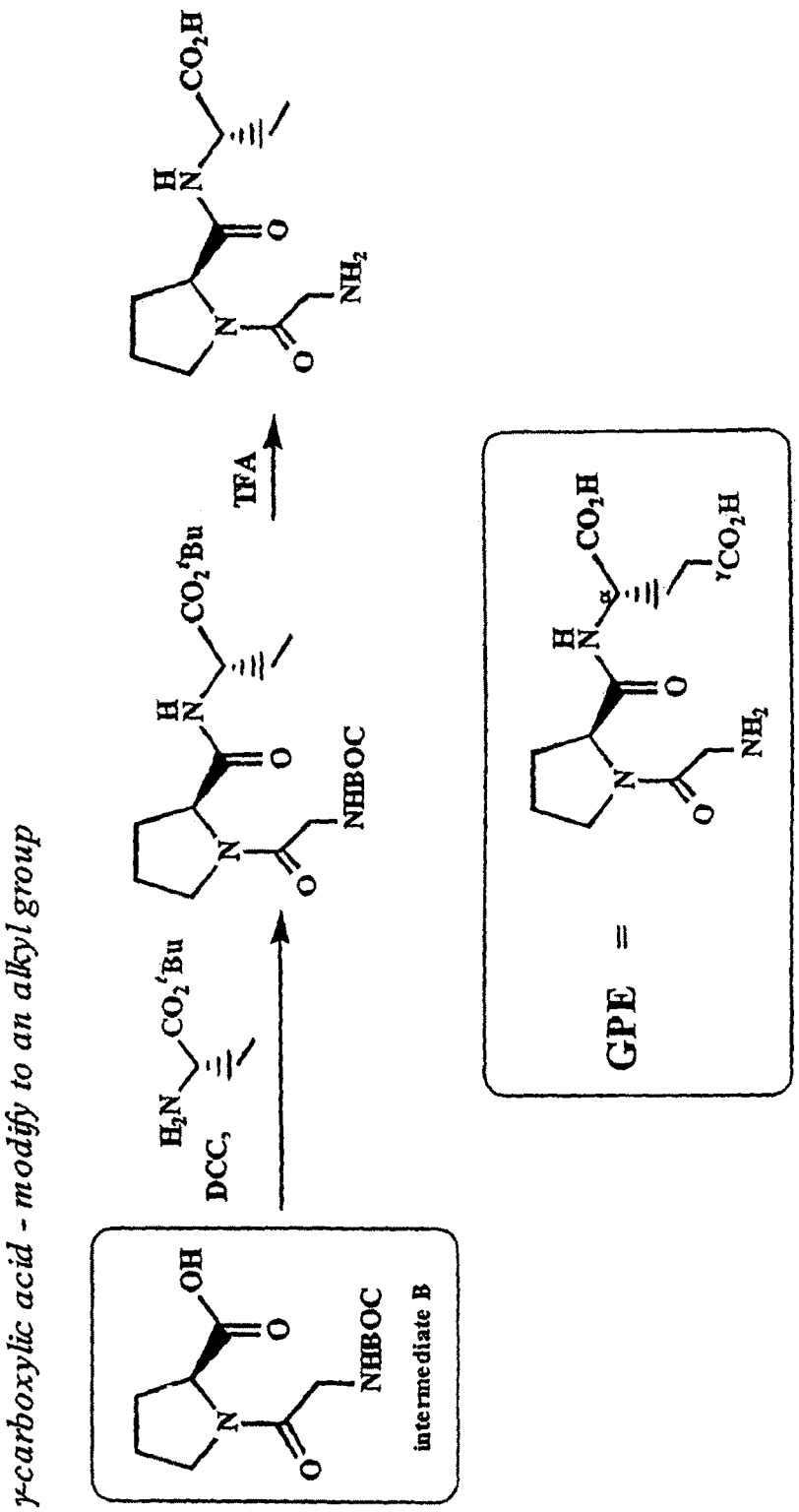
Figure 8:
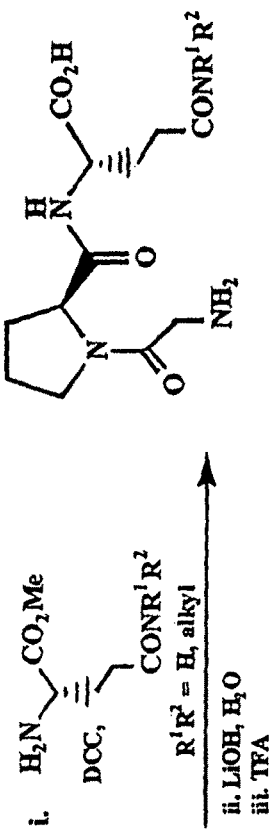
Figure 8:
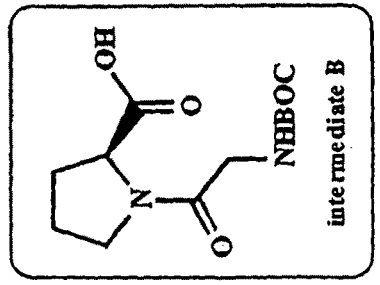
Figure 8:
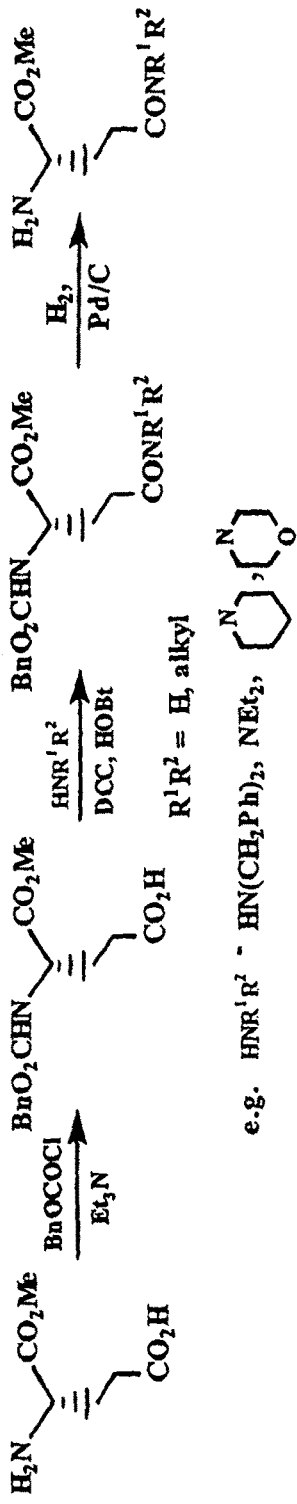
Figure 9:
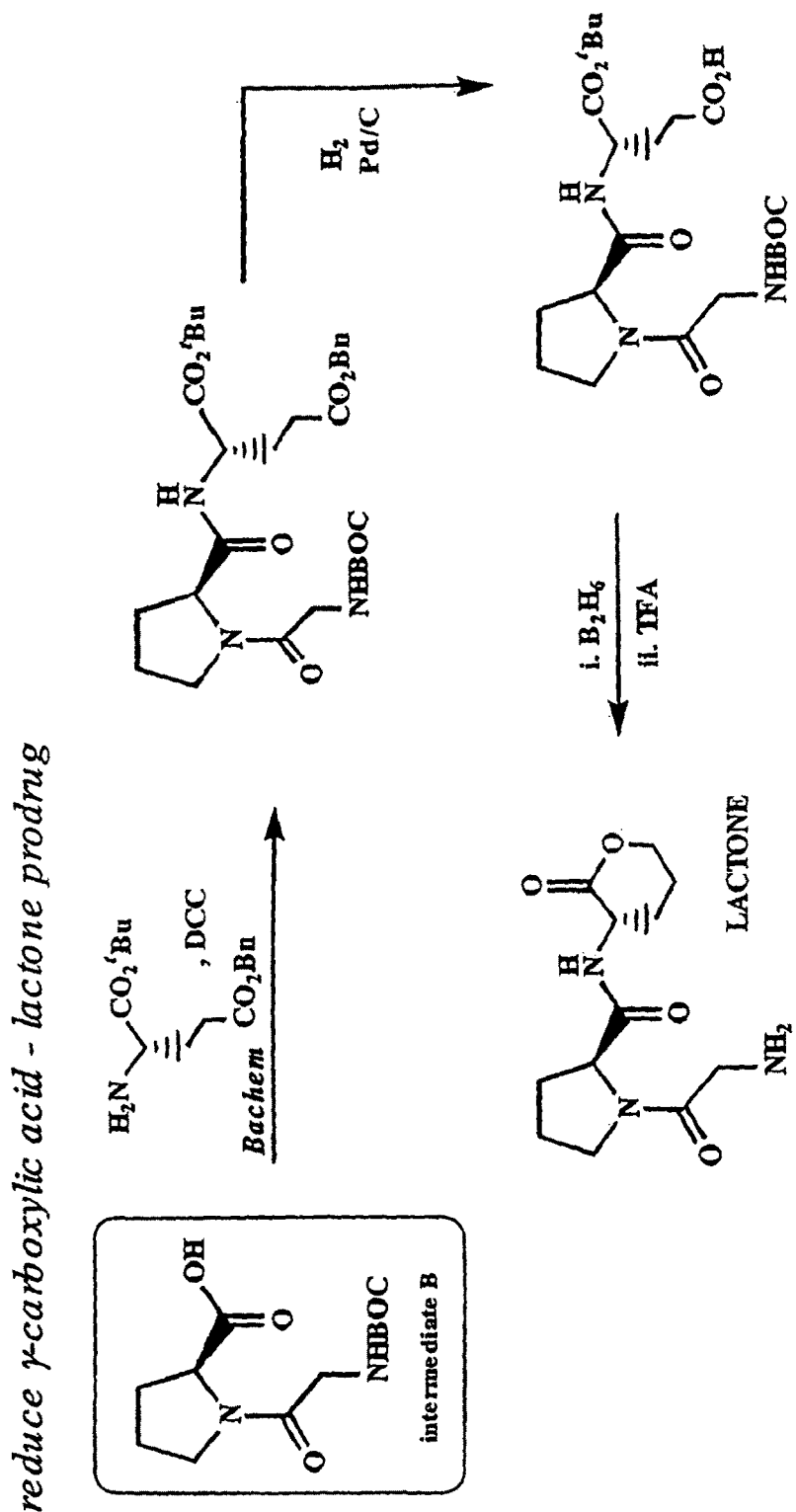
Figure 10:
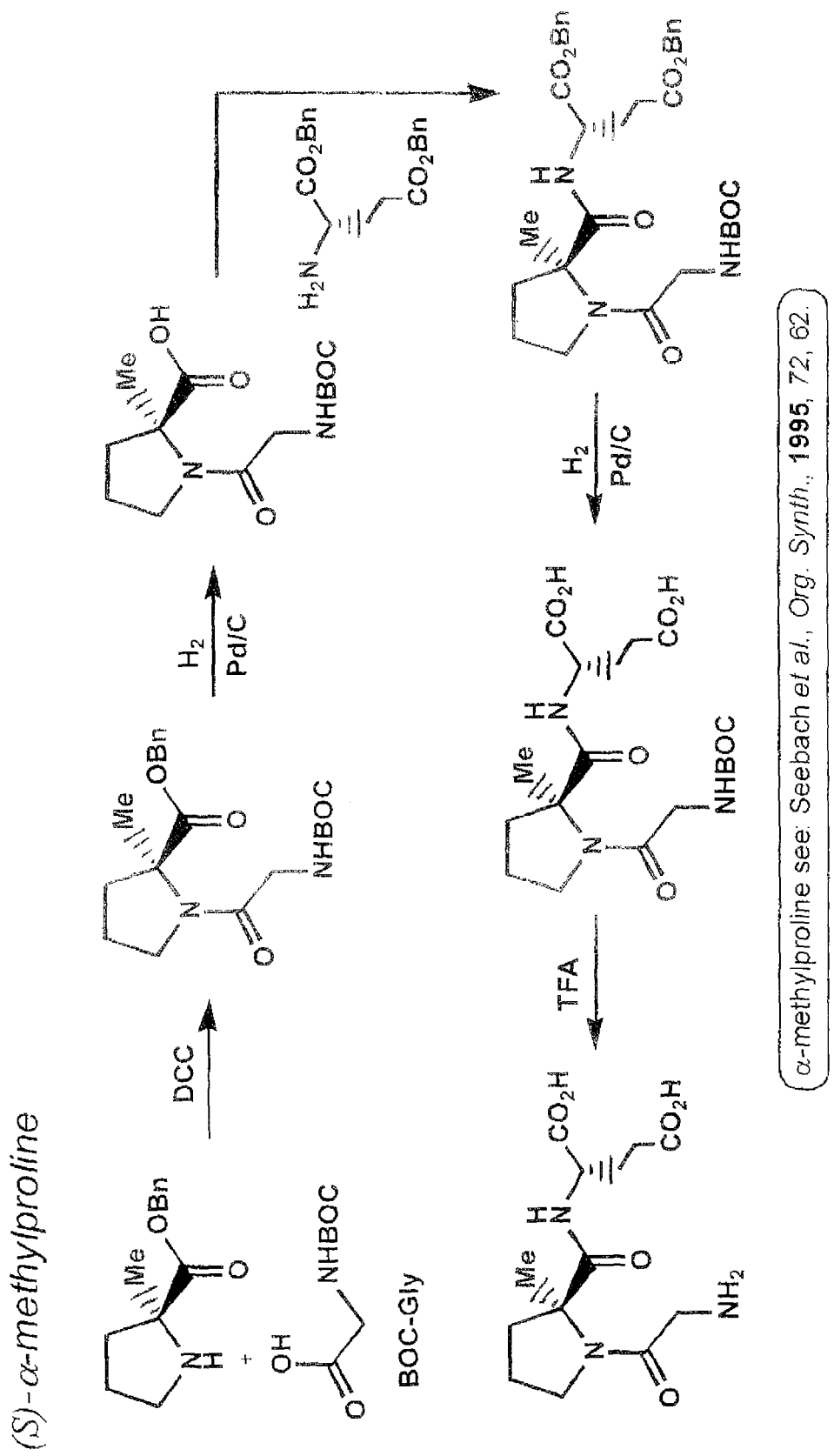
FIGS. 10 and 11 depict schemes for modifying peptide linkages of GPE.
Figure 11:
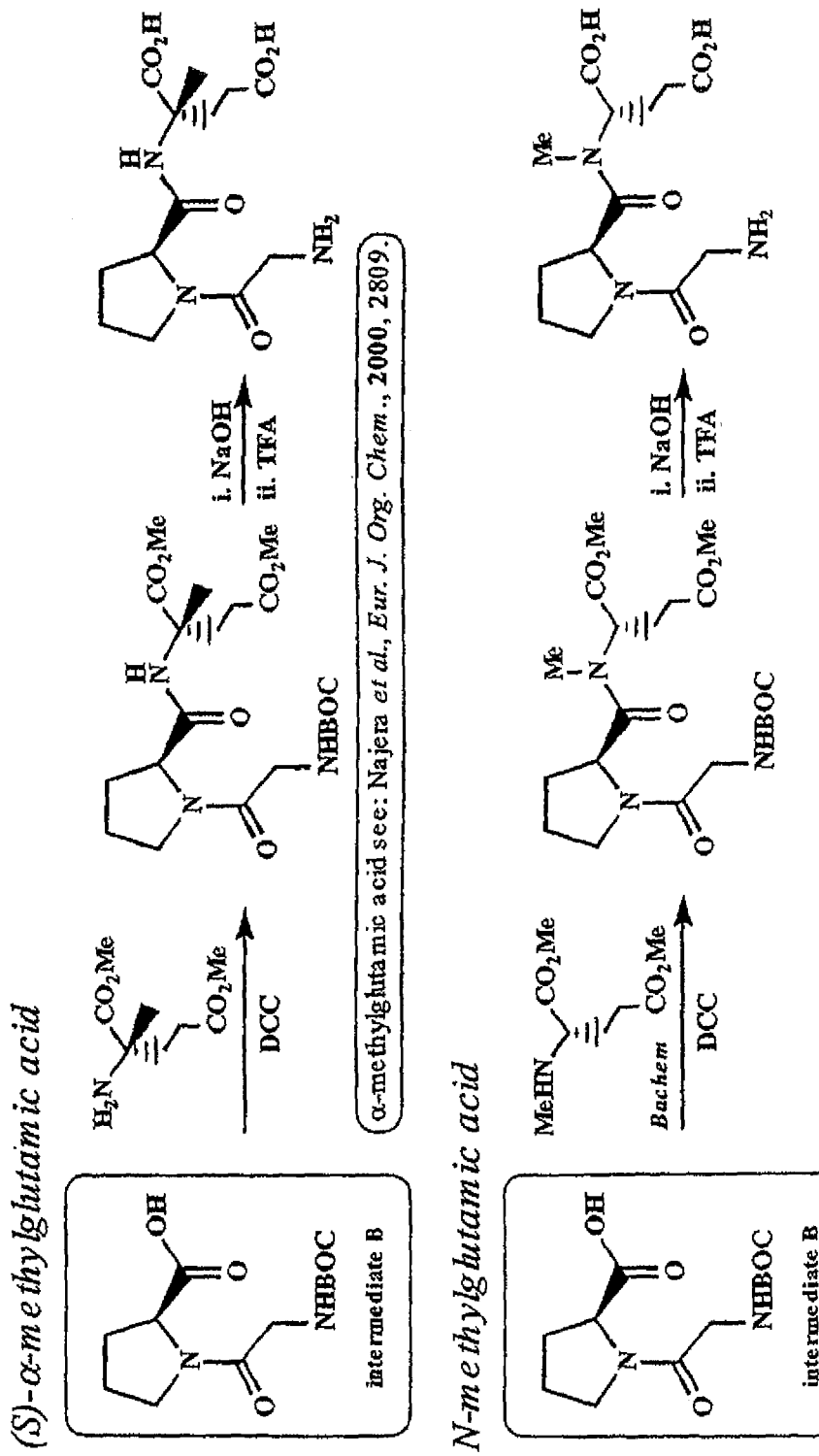
Figure 12:
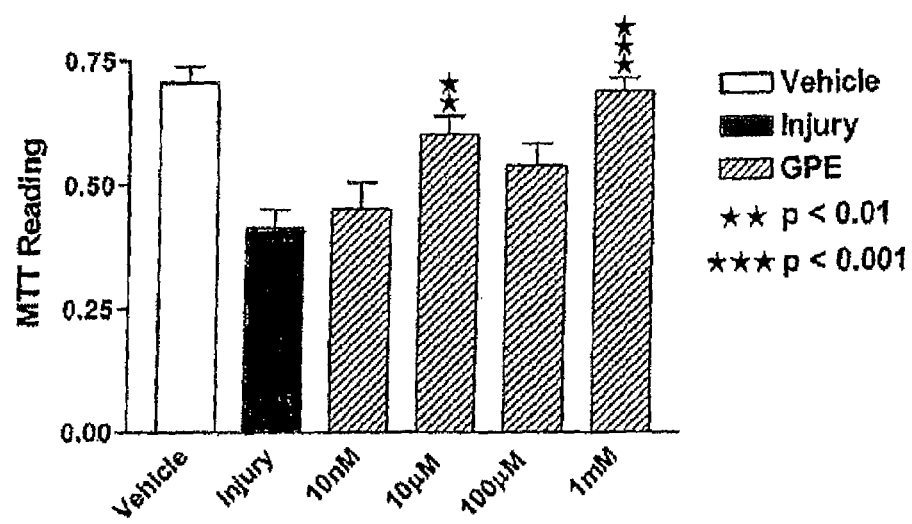
FIGS. 12-15 depict graphs summarizing results of testing neurons in vitro with GPE or G-2MePE and okadaic acid.
Figure 13:
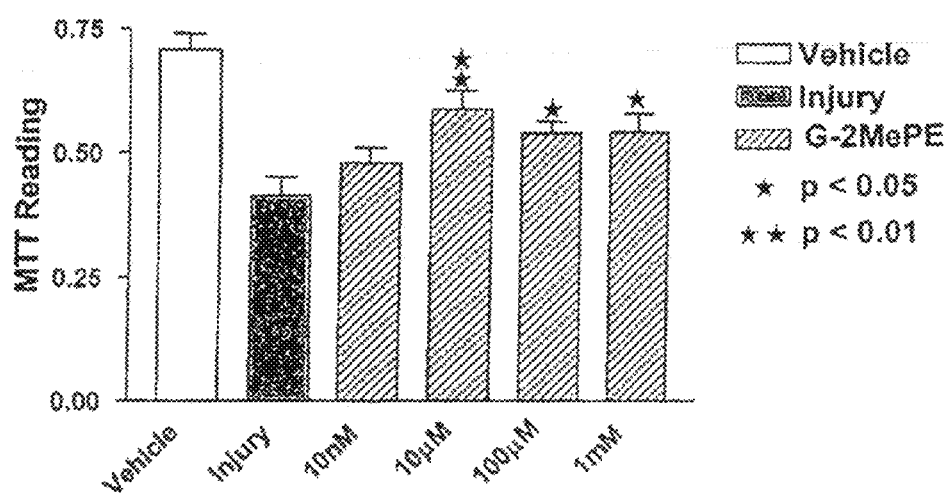

For example, analogs in which the glycine residue of GPE is replaced by an alternative amino acid, or by a non-amino acid, may conveniently be prepared by the preparation of a C-protected proline-glutamic acid dipeptide (such as the dibenzyl ester), and coupling that dipeptide with an N-protected glycine analog, such as BOC-N-methylglycine, BOC-L-valine, N-pyrrolidineacetic acid, and the like, followed by deprotection, as illustrated in FIGS. 2 and 3. Analogs in which the glutamic acid residue of GPE is replaced by an alternative amino acid or an amino acid amide or ester may conveniently be prepared by the preparation of an N-protected glycine-L-proline dipeptide (such as BOC-glycyl-L-proline), and coupling that dipeptide with a C-protected glutamic acid or analog thereof, such as tert-butyl γ-aminobutyrate, methyl 4-amino-4-dimethylcarbamoylbutyrate, L-glutamine methyl ester, dimethyl 1-methylglutamate, etc. Lactones may be prepared by the preparation of an appropriate mono-acid-mono-ester derivative and reduction Analogs in which $R^2$ is alkyl may conveniently be prepared simply by use of the appropriate 2-alkylproline in the synthesis, and similarly analogs in which $R^3$ is alkyl may conveniently be prepared by the use of the appropriate N-alkylglutamic acid or analogue in the synthesis. Where modifications are to be made to two or more amino acids, the coupling techniques will still be the same, with just more than one modified amino acid or analogue being used in the synthesis. The choice of appropriate protecting groups for the method chosen (solid-phase or solution-phase), and of appropriate substrates if solid-phase synthesis is used, will be within the skill of a person of ordinary skill in the art.

Compounds of Formula 2 may be prepared from suitably protected 5-oxo-L-proline or analogs or derivatives thereof, following methods such as the coupling of the proline carboxyl group with a protected glutamic acid or analog or derivative to give an analog of intermediate A of FIG. 2, comparable to the coupling reaction shown in FIG. 2, and then alkylating the pyrrolidine nitrogen with a group of the formula A-$(CH_2)_m$—CH($R^1$)—$CH_2$R, protected at A if necessary, where R is a leaving group under alkylation conditions. Alternatively, the suitably protected 5-oxo-L-proline may first by alkylated at the pyrrolidine nitrogen to give an analog of intermediate B of FIG. 4, and then coupling this with a suitably protected glutamic acid or analog or derivative in the manner shown in FIGS. 4 though 9.

EXAMPLES

The following examples are intended to illustrate embodiments of this invention, and are not intended to limit the scope to these specific examples.

Example 1

Synthesis of
N,N-Dimethylglycyl-L-prolyl)-L-glutamic acid

The following non-limiting example illustrates the synthesis of a compound of the invention, N,N-Dimethylglycyl-L-prolyl-L-glutamic acid

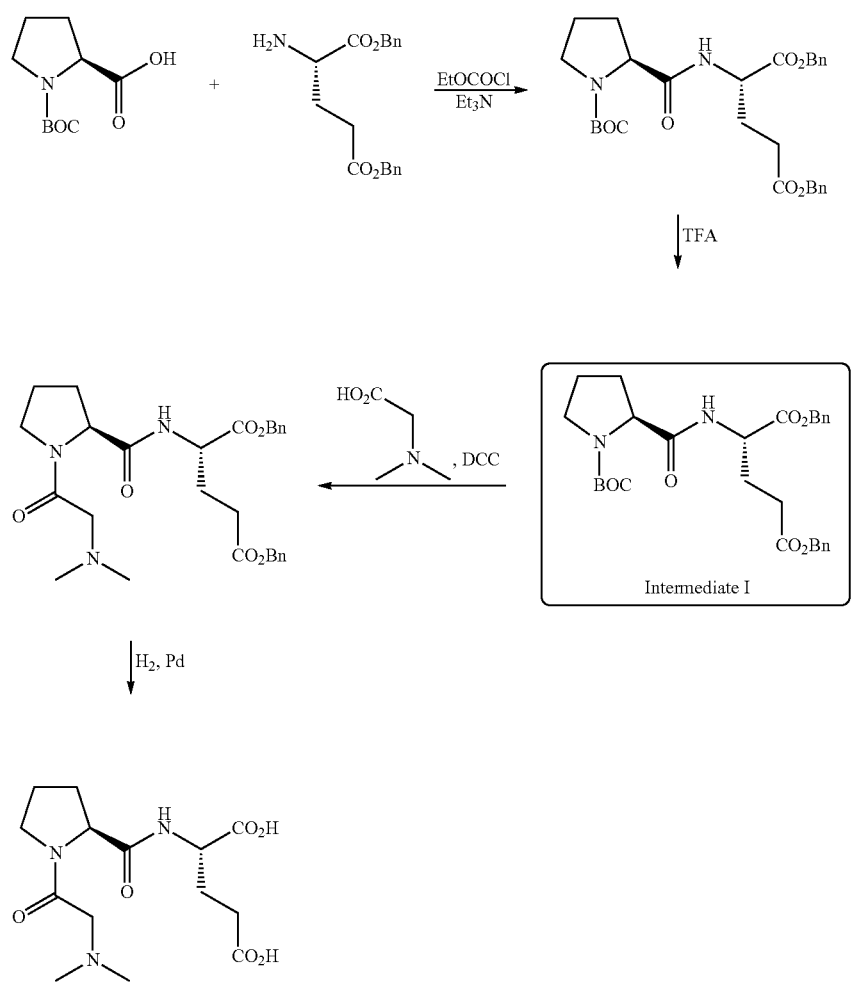

Intermediate I

BOC = $^t$BuOCO

All starting materials and other reagents were purchased from Aldrich; BOC=tert-butoxycarbonyl; Bn=benzyl.

BOC-L-proline-O-benzyl)-L-glutamic acid benzyl ester

To a solution of BOC-proline [Anderson G W and McGregor A C: J. Amer. Chem. Soc.: 79, 6810, 1994] (10 mmol) in dichloromethane (50 ml), cooled to 0° C., was added triethylamine (1.39 ml, 10 mmol) and ethyl chloroformate (0.96 ml, 10 mmol). The resultant mixture was stirred at 0° C. for 30 minutes. A solution of dibenzyl-L-glutamate (10 mmol) was then added and the mixture stirred at 0° C. for 2 hours then warmed to room temperature and stirred overnight. The reaction mixture was washed with aqueous sodium bicarbonate and citric acid (2 mol l$^{-1}$) then dried (MgSO$_4$) and concentrated at reduced pressure to give BOC-L-proline-L-glutamic acid dibenzyl ester (5.0 g, 95%).

L-proline-L-glutamic acid dibenzyl ester

A solution of BOC-L-glutamyl-L-proline dibenzyl ester (3.4 g, 10 mmol), cooled to 0° C., was treated with trifluoroacetic acid (25 ml) for 2 h. at room temperature. After removal of the volatiles at reduced pressure the residue was triturated with ether to give L-proline-L-glutamic acid dibenzyl ester.

N,N-Dimethylglycyl-L-prolyl-L-glutamic acid

A solution of dicyclohexylcarbodiimide (10.3 mmol) in dichloromethane (10 ml) was added to a stirred and cooled (0° C.) solution of L-proline-L-glutamic acid dibenzyl ester (10 mmol), N,N-dimethylglycine (10 mmol) and triethylamine (10.3 mmol) in dichloromethane (30 ml). The mixture was stirred at 0° C. overnight and then at room temperature for 3 h. After filtration, the filtrate was evaporated at reduced pressure. The resulting crude dibenzyl ester was dissolved in a mixture of ethyl acetate (30 ml) and methanol (30 ml) containing 10% palladium on charcoal (0.5 g) then hydrogenated at room temperature and pressure until the uptake of hydrogen ceased. The filtered solution was evaporated and the residue recrystallised from ethyl acetate to yield the tripeptide derivative.

It can be appreciated that following the method of the Examples, and using alternative amino acids or their amides or esters, will yield other compounds of Formula 1.

Example 2

Synthesis of Glycyl-L-2-Methyl-L-Prolyl-L-Glutamate

Glycyl-L-2-Methylprolyl-L-Glutamic Acid (G-2MePE)

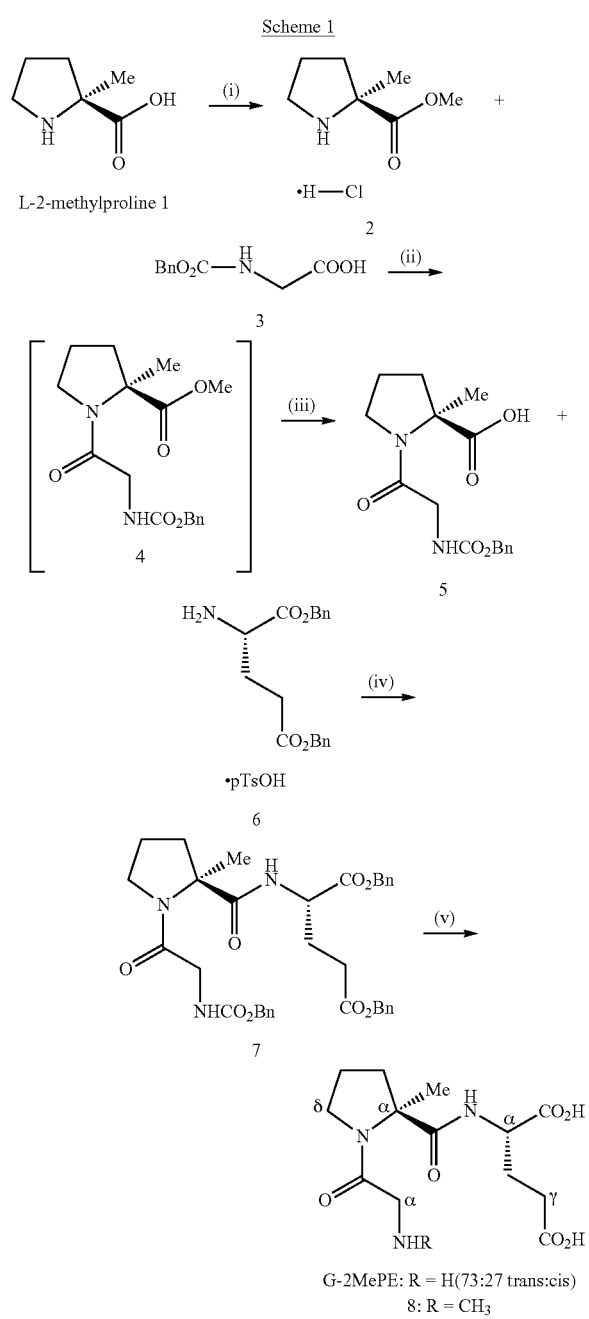

Scheme 1

Reagents, conditions and yields:
(i) SOCl$_2$, MeOH, 79° C. N$_2$, 24 h(104%);
(ii) Et$_3$N, DCC, CH$_2$Cl$_2$, 0° C. to RT, N$_2$, 20 h;
(iii) 1 M aq. NaOH, 1.4-dioxane, 19 h (60%, 2 steps);
(iv) Et$_3$N, BoPCl, CH$_2$Cl$_2$, RT, N$_2$, 17 h (89%);
(v) H$_2$, 10% Pd/C, 91:9 MeOH—H$_2$O, RT, 23 h (86%).

L-2-Methylproline and L-glutamic acid dibenzyl ester p-toluenesulphonate were purchased from Bachem, N-benzyloxycarbonyl-glycine from Acros Organics and bis(2-oxo-3-oxazolidinyl)phosphinic chloride (BoPCl, 97%) from Aldrich Chem. Co.

Methyl L-2-methylprolinate hydrochloride 2

Thionyl chloride (5.84 cm$^3$, 80.1 mmol) was cautiously added dropwise to a stirred solution of (L)-2-methylproline 1 (0.43 g, 3.33 mmol) in anhydrous methanol (30 cm$^3$) at −5° C. under an atmosphere of nitrogen. The reaction mixture was heated under reflux for 24 h, and the resultant pale yellow-coloured solution was concentrated to dryness in vacuo. The residue was dissolved in a 1:1 mixture of methanol and toluene (30 cm$^3$) then concentrated to dryness to remove residual thionyl chloride. This procedure was repeated twice more, yielding hydrochloride 2 (0.62 g, 104%) as an hygroscopic, spectroscopically pure, off-white solid: mp 127-131° C.; $[\alpha]_D$ −59.8 (c 0.24 in CH$_2$Cl$_2$); $\nu_{max}$ (film)/cm$^{-1}$ 3579, 3398 br, 2885, 2717, 2681, 2623, 2507, 1743, 1584, 1447, 1432, 1374, 1317, 1294, 1237, 1212, 1172, 1123, 981, 894, 861 and 764; $\delta_H$ (300 MHz; CDCl$_3$; Me$_4$Si) 1.88 (3H, s, Proα-CH$_3$), 1.70-2.30 (3H, br m, Proβ-H$_A$H$_B$ and Proγ-H$_2$), 2.30-2.60 (1H, br m, Proβ-H$_A$H$_B$), 3.40-3.84 (2H, br m, Proδ-H$_2$), 3.87 (3H, s, CO$_2$CH$_3$), 9.43 (1H, br s, NH) and 10.49 (1H, br s, HCl); $\delta_C$ (75 MHz; CDCl$_3$) 21.1 (CH$_3$, Proα-CH$_3$), 22.4 (CH$_2$, Proγ-C), 35.6 (CH$_2$, Proβ-C), 45.2 (CH$_2$, Proδ-C), 53.7 (CH$_3$, CO$_2$CH$_3$), 68.4 (quat., Proα-C) and 170.7 (quat., CO); m/z (FAB+) 323.1745 [M$_2$.H$^{35}$Cl.H$^+$: (C$_7$H$_{13}$NO$_2$)$_2$.H$^{35}$Cl.H requires 323.1738] and 325.1718 [M$_2$.H$^{37}$Cl.H$^+$: (C$_7$H$_{13}$NO$_2$)$_2$.H$^{37}$Cl.H requires 325.1708].

N-Benzyloxycarbonyl-glycyl-L-2-methylproline 5

Anhydrous triethylamine (0.45 cm$^3$, 3.23 mmol) was added dropwise to a mixture of methyl L-2-methylprolinate hydrochloride 2 (0.42 g, 2.34 mmol) and N-benzyloxycarbonyl-glycine (98.5%) 3 (0.52 g, 2.45 mmol) in methylene chloride (16 cm$^3$), at 0° C., under an atmosphere of nitrogen. The resultant solution was stirred for 20 min and a solution of 1,3-dicyclohexylcarbodiimide (0.56 g, 2.71 mmol) in methylene chloride (8 cm$^3$) at 0° C. was added dropwise and the reaction mixture was warmed to room temperature and stirred for a further 20 h. The resultant white mixture was filtered through a Celite™ pad to partially remove 1,3-dicyclohexylurea, and the pad was washed with methylene chloride (50 cm$^3$). The filtrate was washed successively with 10% aqueous hydrochloric acid (50 cm$^3$) and saturated aqueous sodium hydrogen carbonate (50 cm$^3$), dried (MgSO$_4$), filtered, and concentrated to dryness in vacuo. Further purification of the residue by flash column chromatography (35 g SiO$_2$; 30-70% ethyl acetate-hexane; gradient elution) afforded tentatively methyl N-benzyloxycarbonyl-glycyl-L-2-methylprolinate 4 (0.56 g), containing 1,3-dicyclohexylurea, as a white semi-solid: R$_f$ 0.65 (EtOAc); m/z (EI+) 334.1534 (M$^+$. C$_{17}$H$_{22}$N$_2$O$_5$ requires 334.1529) and 224 (1,3-dicyclohexylurea).

To a solution of impure prolinate 4 (0.56 g, ca. 1.67 mmol) in 1,4-dioxane (33 cm$^3$) was added dropwise 1M aqueous sodium hydroxide (10 cm$^3$, 10 mmol) and the mixture was stirred for 19 h at room temperature. Methylene chloride (100 cm$^3$) was then added and the organic layer extracted with saturated aqueous sodium hydrogen carbonate (2×100 cm$^3$). The combined aqueous layers were carefully acidified with hydrochloric acid (32%), extracted with methylene chloride (2×100 cm$^3$), and the combined organic layers dried (MgSO$_4$), filtered, and concentrated to dryness in vacuo. Purification of the ensuing residue (0.47 g) by flash column chromatography (17 g $SiO_2$; 50% ethyl acetate-hexane to 30% methanol-dichloromethane; gradient elution) gave N-protected dipeptide 5 (0.45 g, 60%) as a white foam in two steps from hydrochloride 2. Dipeptide 5 was shown to be exclusively the trans-orientated conformer by NMR analysis: $R_f$ 0.50 (20% MeOH—$CH_2Cl_2$); $[α]_D$ −62.3 (c 0.20 in $CH_2Cl_2$); $v_{max}$ (film)/$cm^{-1}$ 3583, 3324 br, 2980, 2942, 1722, 1649, 1529, 1454, 1432, 1373, 1337, 1251, 1219, 1179, 1053, 1027, 965, 912, 735 and 698; $δ_H$ (300 MHz; $CDCl_3$; $Me_4Si$) 1.59 (3H, s, Proα-$CH_3$), 1.89 (1H, 6 lines, J 18.8, 6.2 and 6.2, Proβ-$H_AH_B$), 2.01 (2H, dtt, J 18.7, 6.2 and 6,2, Proγ-$H_2$), 2.25-2.40 (1H, m, Proβ-$H_AH_B$), 3.54 (2H, t, J 6.6, Proδ-$H_2$), 3.89 (1H, dd, J 17.1 and 3.9, Glyα-$H_AH_B$), 4.04 (1H, dd, J 17.2 and 5.3, Glyα-$H_AH_B$), 5.11 (2H, s, $OCH_2Ph$), 5.84 (1H, br t, J 4.2, N—H), 7.22-7.43 (5H, m, Ph) and 7.89 (1H, br s, —COOH); $δ_C$ (75 MHz; $CDCl_3$) 21.3 ($CH_3$, Proα-$CH_3$), 23.8 ($CH_2$, Proγ-C), 38.2 ($CH_2$, Proβ-C), 43.6 ($CH_2$, Glyα-C), 47.2 ($CH_2$, Proδ-C), 66.7 (quat, Proα-C), 66.8 ($CH_2$, $OCH_2Ph$), 127.9 (CH, Ph), 127.9 (CH, Ph), 128.4, (CH, Ph), 136.4 (quat., Ph), 156.4 (quat., $NCO_2$), 167.5 (quat., Gly-CON) and 176.7 (quat., CO); m/z (EI+) 320.1368 ($M^+$. $C_{16}H_{20}N_2O_5$ requires 320.1372).

Dibenzyl N-benzyloxycarbonyl-glycyl-L-2-methyl-prolyl-L-glutamate 7

Triethylamine (0.50 $cm^3$, 3.59 mmol) was added dropwise to a solution of dipeptide 5 (0.36 g, 1.12 mmol) and L-glutamic acid dibenzyl ester p-toluenesulphonate 6 (0.73 g, 1.46 mmol) in methylene chloride (60 $cm^3$) under nitrogen at room temperature, and the reaction mixture stirred for 10 min. Bis(2-oxo-3-oxazolidinyl)phosphinic chloride (BoPCl, 97%) (0.37 g, 1.41 mmol) was added and the colourless solution stirred for 17 h. The methylene chloride solution was washed successively with 10% aqueous hydrochloric acid (50 $cm^3$) and saturated aqueous sodium hydrogen carbonate (50 $cm^3$), dried ($MgSO_4$), filtered, and evaporated to dryness in vacuo. Purification of the resultant residue by repeated (2×) flash column chromatography (24 g $SiO_2$; 30-70% ethyl acetate-hexane; gradient elution) yielded fully protected tripeptide 7 (0.63 g, 89%) as a colourless oil. Tripeptide 7 was shown to be exclusively the trans-orientated conformer by NMR analysis: $R_f$ 0.55 (EtOAc); $[α]_D$ −41.9 (c 0.29 in $CH_2Cl_2$); $v_{max}$ (film)/$cm^{-1}$ 3583, 3353 br, 2950, 1734, 1660, 1521, 1499, 1454, 1429, 1257, 1214, 1188, 1166, 1051, 911, 737 and 697; $δ_H$ (400 MHz; $CDCl_3$; $Me_4Si$) 1.64 (3H, s, Proα-$CH_3$), 1.72 (1H, dt, J 12.8, 7.6 and 7.6, Proβ-$H_AH_B$), 1.92 (2H, 5 lines, J 6.7, Proγ-$H_2$), 2.04 (1H, 6 lines, J 7.3 Gluβ-$H_AH_B$), 2.17-2.27 (1H, m, Gluβ-$H_AH_B$), 2.35-2.51 (3H, m, Proβ-$H_AH_B$ and Gluγ-$H_2$), 3.37-3.57 (2H, m, Proδ-$H_2$), 3.90 (1H, dd, J 17.0 and 3.6, Glyα-$H_AH_B$), 4.00 (1H, dd, J 17.1 and 5.1, Glyα-$H_AH_B$), 4.56 (1H, dd, J 7.7 and 4.9, Gluα-H), 5.05-5.20 (6H, m, 3×$OCH_2Ph$), 5.66-5.72 (1H, br m, Gly-NH), 7.26-7.37 (15H, m, 3×Ph) and 7.44 (1H, d, J 7.2, Glu-NH); $δ_C$ (100 MHz; $CDCl_3$) 21.9 ($CH_3$, Proα-$CH_3$), 23.4 ($CH_2$, Proγ-C), 26.6 ($CH_2$, Gluβ-C), 30.1 ($CH_2$, Gluγ-C), 38.3 ($CH_2$, Proβ-C), 43.9 ($CH_2$, Glyα-C), 47.6 ($CH_2$, Proδ-C), 52.2 (CH, Gluα-C), 66.4 ($CH_2$, $OCH_2Ph$), 66.8 ($CH_2$, $OCH_2Ph$), 67.1 ($CH_2$, $OCH_2Ph$), 68.2 (quat, Proα-C), 127.9 (CH, Ph), 128.0 (CH, Ph), 128.1, (CH, Ph), 128.2, (CH, Ph), 128.2, (CH, Ph), 128.3, (CH, Ph), 128.4, (CH, Ph), 128.5, (CH, Ph), 128.5, (CH, Ph), 135.2 (quat., Ph), 135.7 (quat., Ph), 136.4 (quat., Ph), 156.1 (quat., $NCO_2$), 167.3 (quat., Gly-CO), 171.4 (quat., CO), 172.9 (quat., CO) and 173.4 (quat., CO); m/z (FAB+) 630.2809 ($MH^+$. $C_{35}H_{40}N_3O_8$ requires 630.2815).

Glycyl-L-2-methylprolyl-L-glutamic acid (G-2MePE)

A mixture of the protected tripeptide 7 (0.63 g, 1.00 mmol) and 10 wt. % palladium on activated carbon (0.32 g, 0.30 mmol) in 91:9 methanol-water (22 $cm^3$) was stirred under an atmosphere of hydrogen at room temperature, protected from light, for 23 h. The reaction mixture was filtered through a Celite™ pad and the pad washed with 75:25 methanol-water (200 $cm^3$). The filtrate was concentrated to dryness under reduced pressure and the residue triturated with anhydrous diethyl ether to afford a 38:1 mixture of G-2MePE and tentatively methylamine 8 (0.27 g, 86%) as an extremely hygroscopic white solid. Analytical reverse-phase HPLC studies on the mixture [Altech Econosphere $C_{18}$, Si column, 150×4.6 mm, 5 □m; 5 min flush with $H_2O$ (0.05% TFA) then steady gradient over 25 min to MeCN as eluent at flow rate of 1 ml/min; detection using diode array] indicated it was a 38:1 mixture of two eluting peaks with retention times of 13.64 and 14.44 min at 207 and 197 nm, respectively. G-2MePE was shown to be a 73:27 trans:cis mixture of conformers by $^1H$ NMR analysis (the ratio was estimated from the relative intensities of the double doublet and triplet at δ 4.18 and 3.71, assigned to the Gluα-H protons of the major and minor conformers, respectively): mp 144° C.$^Φ$; $[α]_D$ −52.4 (c 0.19 in $H_2O$); $δ_H$ (300 MHz; $D_2O$; internal MeOH) 1.52 (3H, s, Proα-$CH_3$), 1.81-2.21 (6H, m, Proβ-$H_2$, Proγ-$H_2$ and Gluβ-$H_2$), 2.34 (1.46H, t, J 7.2, Gluγ-$H_2$), 2.42* (0.54H, t, J 7.3, Gluγ-$H_2$), 3.50-3.66 (2H, m, Proδ-$H_2$), 3.71* (0.27H, t, J 6.2, Gluα-H), 3.85 (1H, d, J 16.6, Glyα-$H_AH_B$), 3.92 (1H, d, J 16.6, Glyα-$H_AH_B$) and 4.18 (0.73H, dd, J 8.4 and 4.7, Gluα-H); $δ_C$ (75 MHz; $D_2O$; internal MeOH) 21.8 ($CH_3$, Proα-$CH_3$), 25.0 ($CH_2$, Proγ-C), 27.8* ($CH_2$, Gluβ-C), 28.8 ($CH_2$, Gluβ-C), 32.9 ($CH_2$, Gluγ-C), 40.8 ($CH_2$, Proβ-C), 42.7 ($CH_2$, Glyα-C), 49.5 ($CH_2$, Proδ-C), 56.0* (CH, Gluα-C), 56.4 (CH, Gluα-C), 69.8 (quat, Proα-C), 166.5 (quat., Gly-CO), 177.3 (quat., Pro-CON), 179.2 (quat., Gluα-CO), 180.2* (quat., Gluγ-CO) and 180.6 (quat., Gluγ-CO); m/z (FAB+) 316.1508 ($MH^+$. $C_{13}H_{22}N_3O_6$ requires 316.1509).

Example 3

In Vitro Neuroprotection

Therapeutic effects of GPE analogues were examined in a series of experiments in vitro to determine their effects neurodegeneration of neural cells of different origin. The in vitro systems described herein are well-established in the art and are known to be predictive of neuroprotective effects observed in vivo, including effects in humans suffering from neurodegenerative disorders.

Material and Methods

The following experimental protocol followed guidelines approved by the University of Auckland Animal Ethics Committee.

Preparation of Cortical Astrocyte Cultures for Harvest of Metabolised Cell Culture Supernatant One cortical hemisphere from a postnatal day 1 rat was used and collected into 4 ml of DMEM. Trituration was performed using a 5 ml glass pipette and an 18-gauge needle. The cell suspension was sieved through a 100 μm cell strainer and washed in 50 ml DMEM (centrifugation for 5 min at 250 g). The sediment was resuspended in 20 ml DMEM+10% fetal calf serum. The suspension was added into two 25 $cm^3$ flasks (10 ml per flask) and cultivated at 37° C. in the presence of 10% $CO_2$ followed by a change of the medium twice a week. When cells reached confluence, they were washed three times with PBS, adjusted to Neurobasal/B27 and incubated for another 3 days. This supernatant was frozen for transient storage at −80° C.

Preparation of Stratial and Cortical Tissue from Rat E18/E19 Embryos

A dam was sacrificed by $CO_2$-treatment, and then was prepared for caesarean section. After surgery, the embryos were removed from their amniotic sacs and decapitated. The heads were placed on ice in DMEM/F12 medium for striatum and PBS+0.65% D(+)-glucose for cortex.

Striatal Tissue Extraction Procedure and Preparation of Cells

A whole brain was removed from the skull with the ventral side facing upwards in DMEM/F12 medium. The striatum was dissected out from both hemispheres under a stereomicroscope and the striatal tissue was placed into a Falcon tube on ice. Striatal tissue was then triturated using a P1000 pipettor in 1 ml of volume. The tissue was triturated by gently pipetting the solution up and down into the pipette tip about 15 times, using shearing force on alternate outflows. The tissue pieces settled to the bottom of the Falcon tube within 30 seconds. The supernatant containing a suspension of dissociated single cells was then transferred to a new sterile Falcon tube on ice. The tissue pieces were triturated again to avoid excessively damaging already dissociated cells, by over triturating them. 1 milliliter of ice-cold DMEM/F12 medium was added to the tissue pieces in the first tube and triturated as before. The tissue pieces were allowed to settle and the supernatant was removed to a new sterile Falcon tube on ice. The cells were centrifuged at 250 g for 5 minutes at 4° C.

Plating and Cultivation of Striatal Cells

Striatal cells were plated into Poly-L-Lysine (0.1 mg/ml) coated 96-well plates (the inner 60 wells only) at a density of 200,000 cells/cm$^2$ in Neurobasal/B27 medium (Invitrogen). The cells were cultivated in the presence of 5% $CO_2$ at 37° C. under 100% humidity. Medium was changed on days 1, 3 and 6.

Cortical Tissue Extraction Procedure and Preparation of Cells

The two cortical hemispheres were carefully removed by spatula from the whole brain with the ventral side facing upside into a PBS+0.65% D(+)-glucose containing petri dish. Forceps were put into the rostral part (near *B. olfactorius*) of the cortex in order to fix the tissue and two lateral-sagittal oriented cuts were made to remove the paraform and entorhinal cortices. A frontal oriented cut at the posterior end was made to remove the hippocampal formation. A final frontal cut was done a few millimetres away from the last cut in order to get hold of area 17/18 of the visual cortex.

Cortices were placed on ice in PBS+0.65% (+)-glucose and centrifuged at 350 g for 5 minutes. The supernatant was removed and trypsin/EDTA (0.05%/0.53 mM) was added for 8 min at 37° C. The reaction was stopped by adding an equal amount of DMEM and 10% fetal calf serum. The supernatant was removed by centrifugation followed by two subsequent washes in Neurobasal/B27 medium.

The cells were triturated once with a glass Pasteur pipette in 1 ml of Neurobasal/B27 medium and subsequently twice by using a 1 ml insulin syringe with a 22 gauge needle. The cell suspension was passed through a 100 μm cell strainer and rinsed by 1 ml of Neurobasal/B27 medium. Cells were counted and adjusted to 50,000 cells per 60 μl.

Plating and Cultivation of Cortical Cells 96-well plates were coated with 0.2 mg/ml Poly-L-Lysine and subsequently coated with 2 μg/ml laminin in PBS, after which 60 μl of cortical astrocyte-conditioned medium was added to each well. Subsequently, 60 μl of cortical cell suspension was added. The cells were cultivated in the presence of 10% $CO_2$ at 37° C. under 100% humidity. At day 1, there was a complete medium change (1:1—Neurobasal/B27 and astrocyte-conditioned medium) with addition of 1 μM cytosine-1'-D-arabino-furanoside (mitosis inhibitor). On days 2 and 5, ⅔ of the medium was changed.

Cerebellar Microexplants from P8 Animals: Preparation, Cultivation and Fixation

Laminated cerebellar cortices of the two hemispheres were explanted from a P8 rat, cut into small pieces in PBS+0.65% D(+) glucose solution and triturated with a 23 gauge needle and subsequently pressed through a 125 μm pore size sieve. The obtained microexplants were centrifuged (60 g) twice (media change) into serum-free BSA-supplemented STARTV-medium (Biochrom). For cultivation, 40 μl of cell suspension was adhered for 3 hours on a 0.1 mg/ml Poly-L-Lysine coated cover slip placed in 35 mm sized 6 well plates in the presence of 5% $CO_2$ under 100% humidity at 34° C. Subsequently, 1 ml of STARTV-medium was added together with the toxins and drugs. The cultures were monitored (evaluated) after 2-3 days of cultivation in the presence of 5% $CO_2$ under 100% humidity. For cell counting analysis, the cultures were fixed in rising concentrations of paraformaldehyde (0.4%, 1.2%, 3% and 4% for 3 min each) followed by a wash in PBS.

Toxin and Drug Administration to Neural Cells In Vitro and Analysis of Data

To study neuroprotective effects of GPE analogues, we carried out a series of experiments in vitro using okadaic acid to cause toxic injury to neural cells. Okadaic acid is an art-recognized toxin that is known to cause injury to neurons. Further, recovery of neural cells or neural cell function after injury by okadaic acid is recognized to be predictive of recoveries from injuries caused by other toxins.

To cause toxic injury to neurons, we exposed neurons to 1:100 parts of okadaic acid at concentrations of 30 nM or 100 nM and 0.5 mM 3-nitropropionic acid (for cerebellar microexplants only). GPE (1 nM-1 mM) or G-2MePE (1 nM-1 mM) was used at 8 days in vitro (DIV) for cortical cultures and 9 DIV for striatal cultures. The incubation time was 24 hours. The survival rate was determined by a colorimetric end-point MTT-assay at 595 nm in a multi-well plate reader. For the cerebellar microexplants four windows (field of 0.65 mm$^2$) with highest cell density were chosen and cells displaying neurite outgrowth were counted.

Results

The GPE analogue G-2MePE exhibited comparable neuroprotective effects within all three tested in vitro systems (FIGS. 12-15).

Cortical cultures responded to 10 μM concentrations of GPE (FIG. 12) or G-2MePE (10 μM, FIG. 13) with 64% and 59% neuroprotection, respectively.

Figure 14:
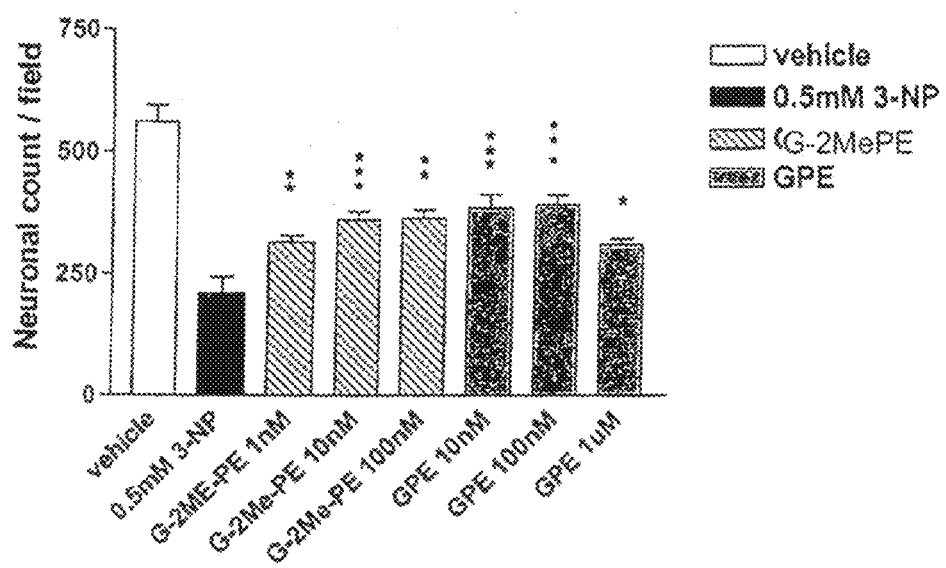
Figure 15:
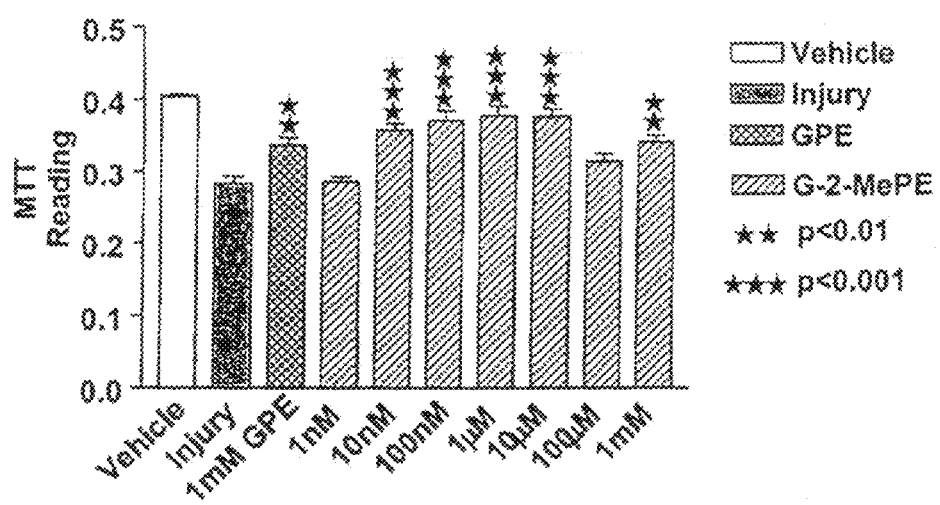

The other 2 types of cultures demonstrated neuroprotection at lower doses of G-2MePE (cerebellar microexplants: FIG. 14 and striatal cells: FIG. 15). Striatal cells demonstrated neuroprotection within the range of 1 nM to 1 mM of G-2MePE (FIG. 15), while the postnatal cerebellar microexplants demonstrated neuroprotection with G-2MePE in the dose range between about 1 nM and about 100 nM (FIG. 14). Thus, we conclude that G-2MePE is a neuroprotective agent and can have therapeutic effects in humans suffering from neurodegenerative disorders. Because G-2MePE can be neuroprotective when directly administered to neurons in culture, that G-2MePE can be effective in vivo when directly administered to the brains of affected animals.

Example 4

Effects of G-2MePE on Striatal Cholinergic Neurons in Aging Rats

To determine whether G-2MePE can affect cholinergic neurons, we studied aging rats. Choline acetyltransferase (ChAT) is an enzyme that is involved in the biosynthesis of the neurotransmitter for cholinergic nerves, acetylcholine. It is well known that immunodetection of ChAT can be used to determine the numbers of cholinergic nerves present in a tissue. It is also known that the numbers of cholinergic nerves present is associated with the physiological function of cholinergic neural pathways in the brain.

In this experiment, we tested the effects of G-2MePE on the number of ChAT-positive neurons in brains of 18-month old rats.

Methods

Eighteen-month old male rats received one of five treatments. A control group was treated with vehicle (saline alone (n=4) and four groups were treated with a single dose of G-2MePE. Doses of 0.012 (n=4), 0.12 (n=5), 1.2 (In=5) and 12 mg/kg (n=3), respectively, were given sub-cutaneously, Rats were sacrificed with an overdose of pentobarbital 3 days after drug treatment. Brains were perfused with normal saline and 4% paraformaldehyde and fixed in perfusion fixative overnight. Brains were stored in 25% sucrose in 0.1M PBS (pH7.4) until the tissue sank, Frozen coronal sections of striatum were cut with a microtome and stored in 0.1% sodium azide in 0.1M PBS at 4° C. Immunoreactivity for choline acetyltransferase (ChAT) was established by staining using a free floating section method. Briefly, antibodies were diluted in 1% goat serum. The sections were incubated in 0.2% triton in 0.1M PBS/Triton™ at 4° C. overnight before Immunohistochemical staining. The sections were pre-treated with 1% $H_2O_2$ in 50% methanol for 20 min. The sections were then incubated with rabbit (Rb) anti-ChAT (1:5000) antibodies (the primary antibodies) in 4D on a shaker for two days. The sections were washed using PBS/Triton™ (15 minutes×3 d) and then incubated with goat anti-rabbit biotinylated secondary antibodies (1:1000) at room temperature overnight. The sections were washed and incubated in ExtrAvidin™ (Sigma) (1:1000) for 3 hours and followed by $H_2O_2$ (0.01%) in 3,3-diaminobenzine tetrahydrochloride (DAB, 0.05%) to produce a coloured reaction product. These sections were mounted on chrome alum-coated slides, dried, dehydrated and covered.

The striatal neurons in both hemispheres exhibiting specific immunoreactivities corresponding to ChAT were counted using a light microscope and a 1 mm 2×1000 grid. The size of the striatal region used for the count was measured using an image analyser. The total counts of neurons/mm² were compared between the groups.

Figure 16:
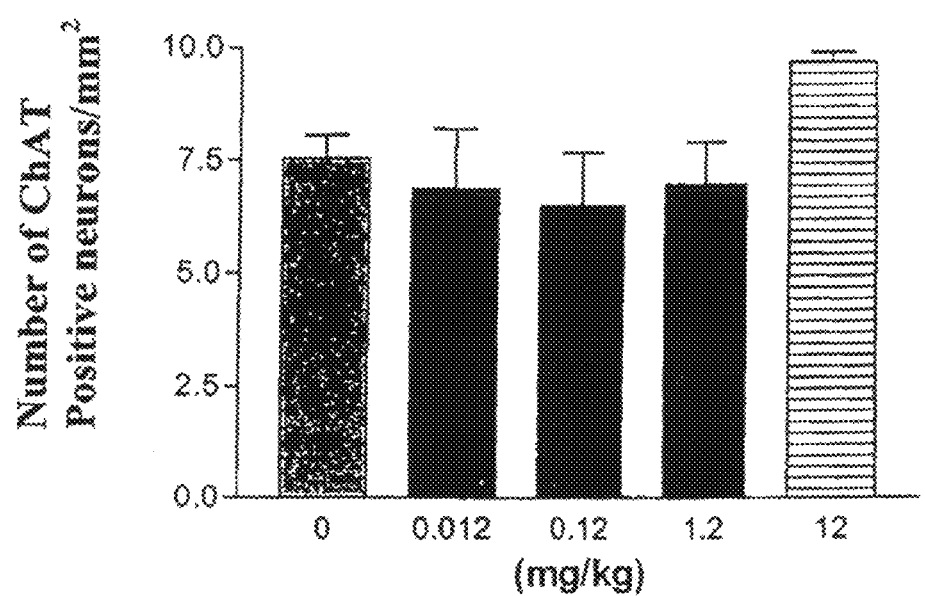
FIG. 16 shows the effects of subcutaneous injection of G-2MePE (at doses of 0.012, 0.12, 1.2 and 12 mg/kg) on the number of ChAT-positive neurons in the striatum of 18-month old rats.

Data were analysed using a paired t-test and presented as mean+/−SEM. Results are presented in FIG. 16.

Results

FIG. 16A shows that the number of ChAT-immunopositive neurons increased in the brains of animals treated with G-2MePE. This clearly indicates that administration of G-2MePE is effective in increasing the level of ChAT in the brains of aged rats. Because ChAT is an enzyme involved in the synthesis of the cholinergic neurotransmitter acetylcholine, we conclude that G-2MePE can increase the amount of cholinergic transmitter in the brains of middle-aged rats.

Example 5

Effects of G-2-MePE on Spatial Reference Memory in Rats

Having demonstrated that G-2-MePE can increase ChAT and therefore has the potential to improve cholinergic neural function, we then examined whether G-2MePE can be useful in treating age-related changes in cognition and/or memory. Therefore, we carried out a series of studies in rats using well-established tests for memory.

Experiment 1: The Morris Water Maze Test

The Morris water maze test is a well-recognized test to assess spatial reference memory in rats.

Subjects

We used male Wistar rats 12, 8 or 4 months of age.

Methods

Testing Environment and Apparatus

The Morris water maze test was conducted using a black plastic pool filled to a depth of 25 cm with water coloured black with a non-toxic dye. The pool had a circular black insert so that the walls also appeared uniform black The pool was divided into four quadrants (north, south, east and west) by two imaginary perpendicular lines crossing at the pool's center A metal platform was placed in the geographical centre of the SE quadrant 50 cm from the edge of the pool, so that it was 2 cm below the water surface and invisible. The platform remained in that position though the training.

The experiment used extra-maze cues (i.e. objects in the room surrounding the pool) that the rats could use to navigate to the platform. Distinctive posters or paintings were hung on the walls. Furniture in the room was not moved during the testing period. The placement of the pool allowed the experimenter an easy access to it from all sides. The pool was emptied and refilled daily during testing, with water at 25° C.+/−2° C.

The furthermost point in the pool (relative to the position of the experimenter) was designated as "north", and the other compass points "east", "south" and "west" were the right-most, bottom and left-most points of the pool respectively. These points were marked with tape on the outside of the pool.

Acquisition Phase

Rats in each group were trained to swim to the submerged platform. The rats received six 60-second trials per day for four consecutive days. A trial began by placing the rat into the water facing the wall of the pool, at one of four start locations (north, south, east, west). The sequence of start locations was chosen pseudorandomly, so that the start location of any given trial was different from that of the previous trial, and no start location was used more than twice during daily training. The same sequence of locations was used for all the rats on a given day but varied between days. The trial ended when the rat had found the platform, or in 60-seconds, which ever occurred first. The trials were timed with a stop watch. If the rat found the platform, it was allowed to remain there for 15-seconds before being removed to a holding container. If the platform was not found, the rat was guided there manually and placed on the platform for 15-seconds. The inter-trial interval was 60-seconds. The holding container was covered in order to minimize any inter-trial interference. At the completion of daily testing for a rat, the animal was towel-dried and placed under the heat lamp in the holding bucket until his coat was dry. The time needed to locate the platform (latency, secs) was obtained for each rat in each training trial. If the rat did not find the platform in a given trial their latency score was the maximum length of that trial (60-seconds).

Drug Treatment

Three days after the completion of the acquisition phase, mini-osmotic pumps (Alzet) were implanted subcutaneously under halothane anaesthesia) to dispense drug or vehicle continuously for 1- or 3-weeks. At the completion of the infusion the pumps were removed and the wounds re-sutured.

The 5 treatment groups were:
1. saline 1-week (n was originally 7, but one rat that lost weight rapidly was excluded and later found to have had a pituitary tumour);
2. saline 3-weeks (n=8);
3. G-2MePE low dose (0.96 mg/day) 1 week (n=8);
4. G-2MePE low dose (0.96 mg/day) 3-weeks (n=8);
5. G-2MePE high dose (4.8 mg/day) 3-weeks (n=7).

The four (n=3) and eight month old (n=9) control rats received no drug treatment. The 12-month old rats were assigned to one of five groups on the basis of their swim times over acquisition, such that the groups were approximately equivalent in their mean performance prior to receiving any drug.

Retention (Reference Memory) Phase

The ability of the rats to remember or to relearn the original platform location was tested four weeks after original training. This means that residual drug would have been washed out for a minimum of 7-days in the case of the 3-week pumps, and 21-days in the case of the 1-week pumps. The retention testing procedure was identical to that of acquisition. Pharmacokinetic studies indicate that the plasma concentration of subcutaneously administered G-2-MePE rose to a peak and then declined with an approximately first order kinetic pattern, with a plasma half-life (t ½) of between about 30 and 60 minutes. Thus, by the time the retention study was performed, at least 7 days after removal of the G-2-MePE containing minipumps, nearly all of the G-2-MePE had been cleared from the animals' circulation.

Data Analysis

The swim latency for each rat was recorded for each trial for each day of the acquisition and retention phases and changes between phases were examined using Analysis of Variance.

The 3-week vehicle and 3-week high dose G-2MePE were compared in acquisition and retention. The high dose of G-2MePE, given over 3 weeks improved the retention of the original water maze task after a 4-week delay.

Results

Figure 17:
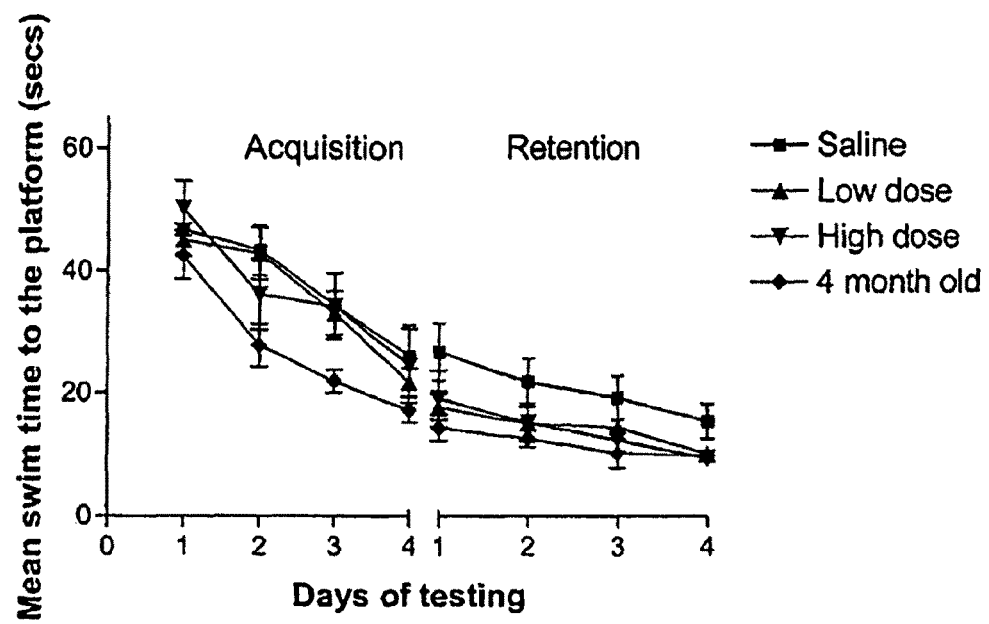
FIG. 17 shows effects of G-2MePE treatment on spatial memory retention in middle-aged 12-month old rats.

FIG. 17 shows the comparison between high-dose (4.8 mg/day) G-2MePE-treated and low-dose-treated (0.96 mg/day) aged rats and saline treated aged rats, with the young controls (4 months) used as controls. Prior to treatment with G-2MePE, there were no differences between the aged (12-month old) groups. In contrast, the 4-month old animals required less time to reach the platform than older animals. After a 3-week period of no testing, during which time either saline or G-2MePE were administered, animals that received saline only did not show improved ability to reach the platform, as indicated by the similar times required at test day 4 of the acquisition phase and test day 1 of the retention phase. In contrast, animals that received treatment with G-2MePE at either the high or low doses, had improved memory as reflected in a decrease in the time needed to reach the platform compared to saline-treated controls. Further, the G-2MePE-treated animals had similar performance to the 4-month old young animals (FIG. 17) and 8-month old animals (data not shown). Thus, we conclude that G-2MePE can improve memory in middle-aged rats animals that had previously shown memory deficits in relation to young rats. Further, because by the time of retesting, the G-2MePE had washed out from the circulation, we conclude that the memory-enhancing effects of 0-2MePE were likely due to the improvement in function of cholinergic neurons.

Experiment 2: 8-Arm Radial Maze Test

Five months after the original experiment the now 17-month old rats were retested for spatial working memory in a radial arm maze.

Methods

Apparatus

The apparatus consists of a central platform communicating with 8 identical arms, each with a food cup (dimensions?) at the end of the arm Testing Procedure Rats were partially food-deprived for at least 10 days prior to, and throughout the radial maze procedure.

The maze was assembled and positioned so that the experimenter could clearly observe the rats' behaviour from a predetermined location. The experimenter numbered the arms of the maze according to their orientation from one to eight in a clock-wise direction.

Pre-Training (Pre-Drug)

On day one the doors were inserted into the arms and each rat was confined in the central platform with 20 food pellets for 5 minutes. This continued once a day for four days, and all of the rats were observed to consume some of the pellets. The following day the rats were allowed five minutes to explore the whole maze. All arms were baited with two food pellets in the food cup located at the end of each arm, and one pellet at both the entrance and middle of each arm. This was repeated for at least five, but up to eight days for rats that explored fewer than eight arms in two consecutive sessions. All rats had a final session on the ninth day of pre-training. At this point it was decided that one of the old rats that had made only one arm entry on eight of the nine days should be excluded from future testing in this procedure. Otherwise all rats were included regardless of the amount of exploring they performed in pre-training. There was no statistically significant difference between the old groups in the number of arms entered on the final pre-training session (Drug: $F(2,31)=0.44$, $p=0.65$).

Drug Treatment 30 days before the test (five days after pre-training) the 17 Male Wistar month old rats were implanted (under halothane anaesthesia) with sub-cutaneous mini-osmotic pumps (Alzet) to dispense drug continuously for 3 weeks. At the completion of the infusion the pumps were removed and the wounds resutured (9-day washout allowed).

The treatment groups were:
1. young controls (4 months old), n=6;
2. saline n=10;
3. G-2MePE low dose (2.4 mg/kg/day) n=13
4. G-2MePE high dose (12.4 mg/kg/day) n=5

Saline and the low dose groups are comprised of all the rats that received those treatments in phase 1 of this experiment (when the rats were 12 months old) regardless of whether they had the one or three week treatment. One rat in each of the saline and high dose groups have been dropped because of skin tumours. One of the low dose rats did not participate in this experiment due to the fact that it could not be pre-trained (see below).

Testing (Post-Drug)

Working memory testing commenced on the ninth day of washout. Rats received 10 daily training sessions over 12 days. The procedure was the same as for pre-training but only the food cups were baited. Rats had 6-mins to make up to 16 choices by visiting any of the eight arms. A choice was defined as occurring when all four paws were inside an arm.

The experimenter recorded the sequence of arm entries with pen and paper. Sessions were terminated after all eight arms had been entered, 16 choices made, or 6-mins had elapsed. The time taken to enter all eight arms, when this occurred, was recorded.

Data Analysis

An arm choice was considered correct when the rat entered an arm not previously visited. Performance was classified daily according to the following parameters:

1) Correct Choice (CC) 8-12 is the number of correct choices made divided by the total number of choices made. For animals that failed to visit all 8 arms in a test, the denominator of this ratio is considered to be 12.

2) Working Correct Choice (WCC) 8-12 is the measure from which the working memory data is derived. Data was collected as described for CC 8-12 above, but for this parameter, only the rats that entered all 8 arms in a session were included.

Rats that made fewer than 8 arm entries were not used to ascertain working memory because they couldn't remember which arms they had previously visited and therefore had memory so impaired that they couldn't complete the, as opposed to the animals that, for whatever reason, did not explore the maze.

Results

CC8-12: There was a general improvement by all of the groups across the 10 days ($F(9,324)=4.01$, $p<0.0001$), but no significant group effect ($F(3,36)=1.19$, ns) or Group X Days interaction ($F(27,324)=1.05$, ns) (data not shown)

Figure 18A:
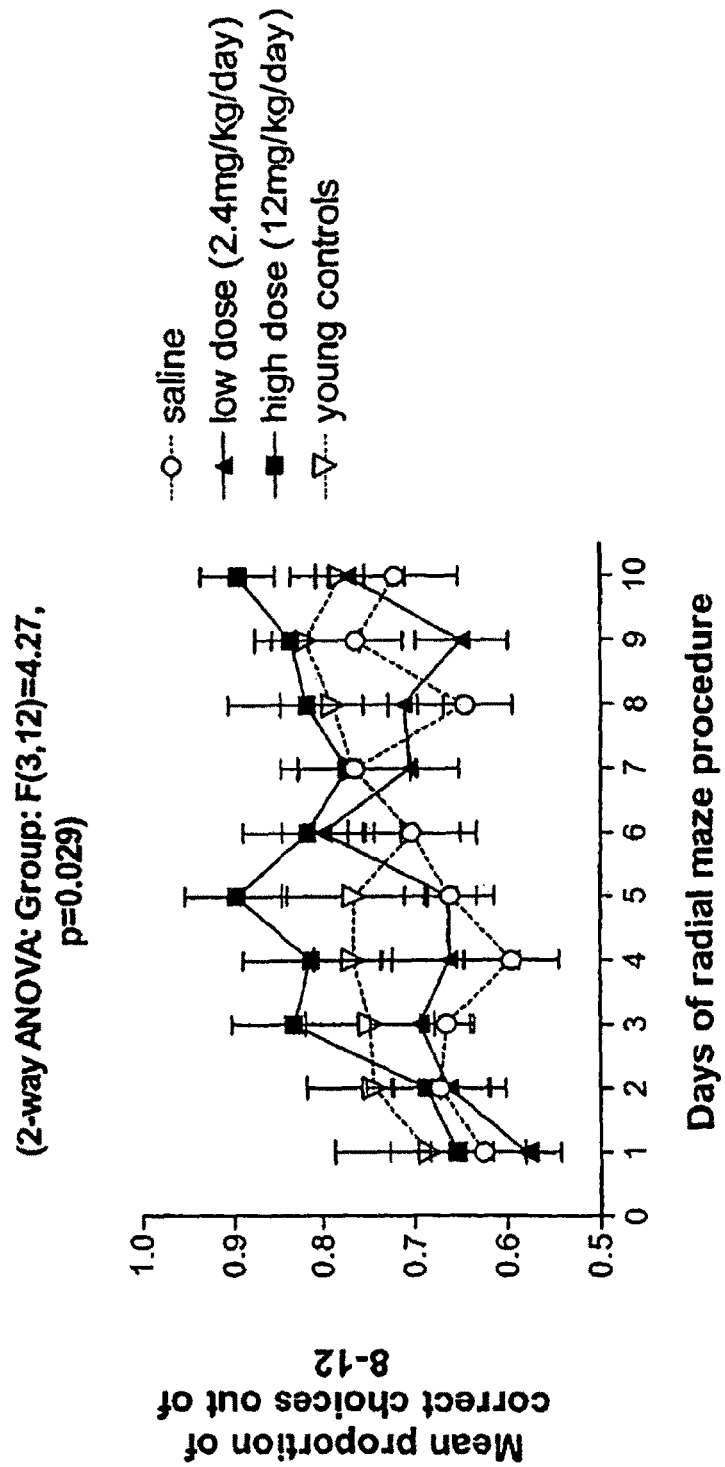
FIGS. 18A and 18B show effects of G-2MePE on spatial working memory of aged (17-month old) rats in an 8-are radial maze following 3-weeks of treatment and a nine day washout.

WCC8-12: FIG. 18A shows the acquisition profile according to WCC8-12 score across the 10 days of testing. There was a significant effect of Group ($F(3,12)=4.27$, $p=0.029$) and Days ($F(9,108)=2.09$, $p=0.036$) but the interaction between these factors was not significant ($F(27,108)=1.06$, ns). The high dose G-2Me-PE group showed the greatest improvement across days, followed by the young controls. There was very little difference between the low dose G-2Me-PE and saline.

Figure 18B:
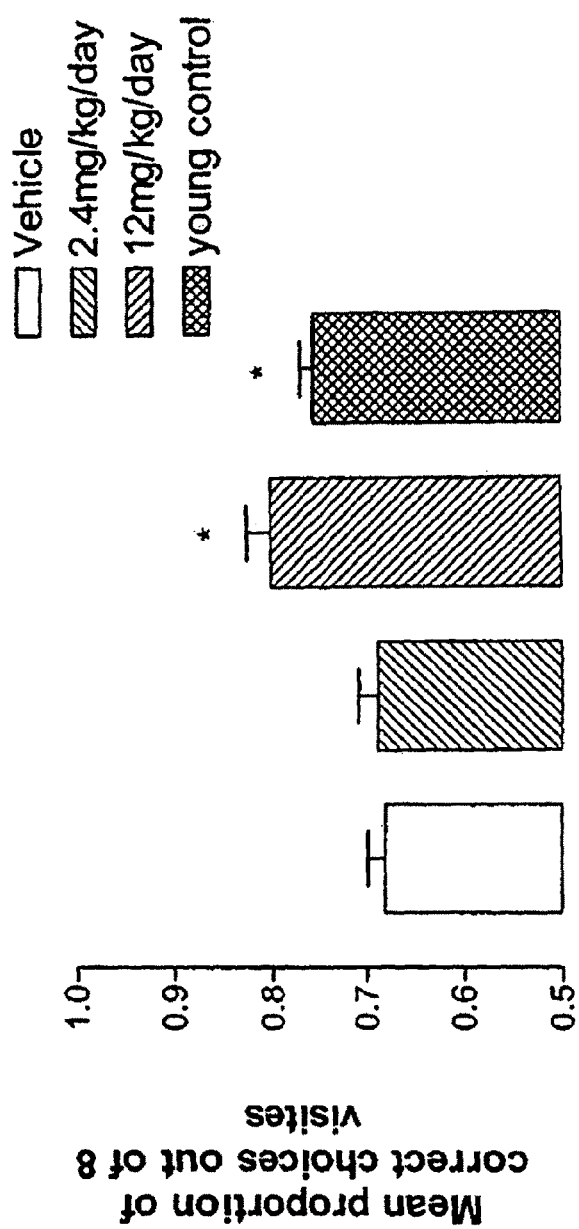

FIG. 18B shows results indicating that rats exposed to the higher dose of G-2MePE (n=5) had made more correct entries for getting food pellets compared to the vehicle treated rats (*$p<0.05$, n=10). We conclude from this study that G-2MePE improves spatial memory in aged rats.

Example 6

G-2MePE Increases Neuroblast Proliferation and Decreases Astrocytosis in Brains of Aged Rats Because neuronal degeneration can result in decreased numbers of neurons, one desirable therapeutic aim is increasing the numbers of neurons in the brain. Neurons are derived from neuroblasts, a less differentiated cell than an neuron, but within the neural lineage. Typically, a neuroblast is exposed to conditions that cause it to mature into a mature phenotype, having a defined soma, neural processes (axons and dendrites) and ultimately, making connections with other neurons (e.g., synapses). Thus, measuring neuroblast proliferation has become a well-known early marker for nerve cell proliferation. Thus, detecting an increase in neuroblast proliferation induced by a pharmaceutical agent is an accepted method for predicting growth of neural cells in animals. Because rats and humans share similar mechanisms in neural cell proliferation, detection of changes in neuroblast proliferation in rats in vivo is predictive of similar effects in human beings.

It is also known that one histological correlate of impaired cognitive function is an increase in the numbers of astrocytic cells in the brain of affected animals. Thus, to determine whether G-2MePE might be useful in stimulating neuroblast proliferation and in treating astrocytosis, we carried out a series of studies in aging rats.

Methods and Materials

Immunohistochemistry

To carry out these studies, tissues were fixed and embedded in paraffin and sections obtained using standard methods. Coronal sections (6 μm) containing the level of the hippocampus were cut and mounted on chrome-alum-coated slides for staining. The sections were deparaffinized in xylene, dehydrated in a series of ethanol and incubated in 0.1 M phosphate buffered saline (PBS).

Primary antibodies against glial fibrillary acidic protein (GFAP) and proliferating cell nuclear antigen (PCNA) were used to mark reactive glial cells and cells undergoing apoptosis and proliferation, respectively. For antigen unmasking (caspase-3 and PCNA staining), sections were heated in 10 mM sodium citrate buffer (pH 6.0) for 1 min at high power. All sections were pretreated with 1% $H_2O_2$ in 50% methanol for 30 min to quench the endogenous peroxidase activity. Then either 1.5% normal horse serum or 2.5% normal sheep serum in PBS was applied for 1 h at room temperature to block nonspecific background staining. The sections were then incubated with following primary antibodies: monoclonal mouse anti-GFAP antibody (Sigma, St. Louis, Mo., U.S.A. diluted 1:500); mouse anti-PCNA antibody (DAKA, A/S, Denmark, diluted 1:100). After incubation with primary antibodies at 4° C. for 2 d (except for PCNA staining which was incubated overnight) the sections were incubated with biotinylated horse anti-mouse or goat anti-rabbit secondary antibody (1:200, Sigma) at 4° C. overnight. The ExtrAvidin™ (Sigma, 1:200), which had been prepared 1 h before use, was applied for 3 h at room temperature, and then reacted in 0.05% 3,3-diaminobenzidine (DAB) and PBS to produce a brown reaction product. Sections were dehydrated in a series of alcohols to xylene and coverslipped with mounting medium.

Immunohistochemical staining was performed on brain samples taken from both control and G-2MePE treated groups of young (4 months old), middle-aged (9 months old) and aged rats (18 months old).

Control sections were processed in the same way except the primary antibody was omitted from the incubation solution. The number of PCNA positive cells was counted in the subventricular zone and the GFAP positive cells was scored in the cerebral cortex.

Experiment 1: G-2MePE Stimulates Neuroblast Proliferation in Brains of Aged Rats The subventricular zone (SVZ) and the dentate gyrus (DG) are two brain regions hosting adult neurogenesis. The reduction of neurogenesis in both SVZ and the DG has been well reported to be co-related to the memory decline with aging and effects of Nerve Growth Factor and Epidermal Growth Factor on memory improvement are reported to be due to increase in progenitors proliferation of the SVZ. Using PCNA as a marker of cell proliferation, cellular proliferation in the SVZ was examined by counting the numbers of cells that are positive for PCNA. In selected animals, at least some of the proliferating cells were identified as neuroblasts, as stained with the neural-cell specific agent, doublecortin.

Figure 19A:
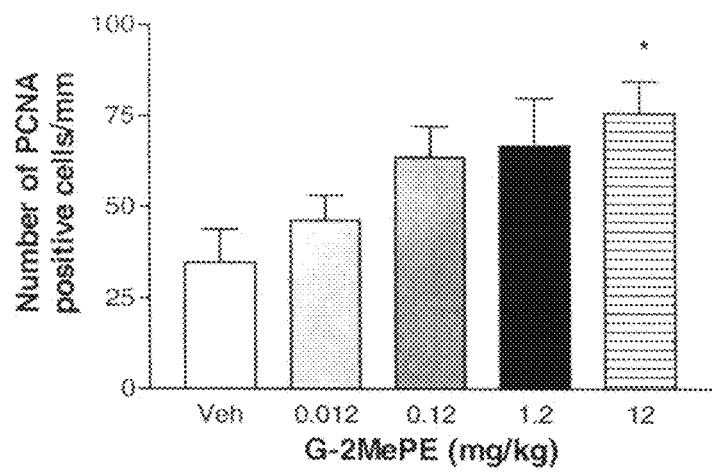
FIG. 19A shows effects of a single intraperitoneal administration of 4 doses of G-2MePE on neuroblast proliferation as assessed by the number of PCNA positive cells in the subventricular zone (SVZ) of aged rats.

Eighteen-month old male rats were treated intraperitoneally with single doses of G2-MePE (doses of either 0, 0.012, 0.12, 1.2, 12 mg/kg). Brains were collected 3 days after the treatments and the immunohistochemical staining of PCNA and GFAP were performed. The number of PCNA positive cells was counted in the SVZ and the number of cells was then averaged as cells/mm depending on the length of ventricle wall used for counting (FIG. 19A). The group treated with highest dose (12 mg/kg, n=5) showed a significant increase in the number of PCNA positive cells compared to the group treated with vehicle (*p<0.05, n=7). The data indicated a dose-dependent effect of G-2PE on improving neurogenesis.

Figure 19B:
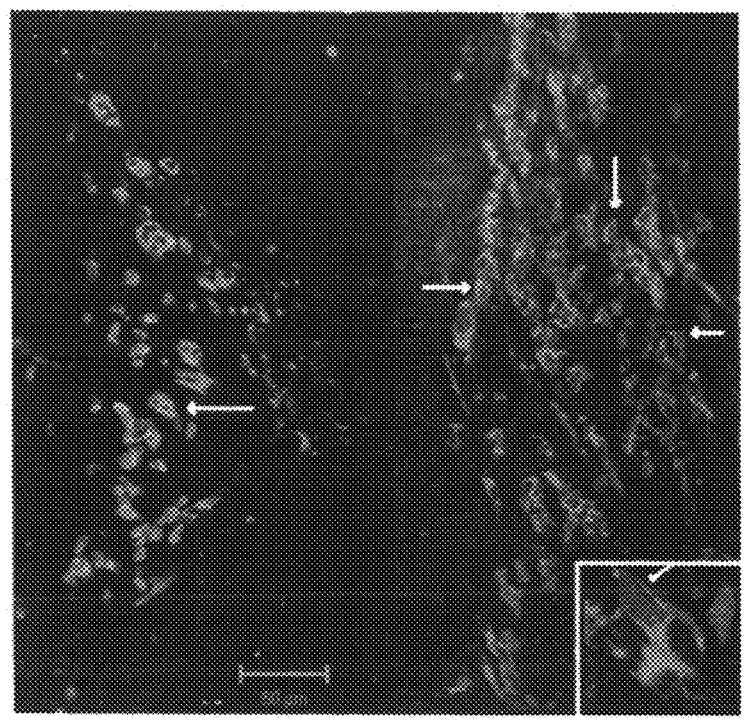
FIG. 19B shows effects of a single intraperitoneal administration of 4 doses of G-2MePE on co-localisation of PCNA and doublecortin staining a rat treated with the highest dose of G-2MePE (right panel) compared to the vehicle treated rat (left panel).
Figure 19C:
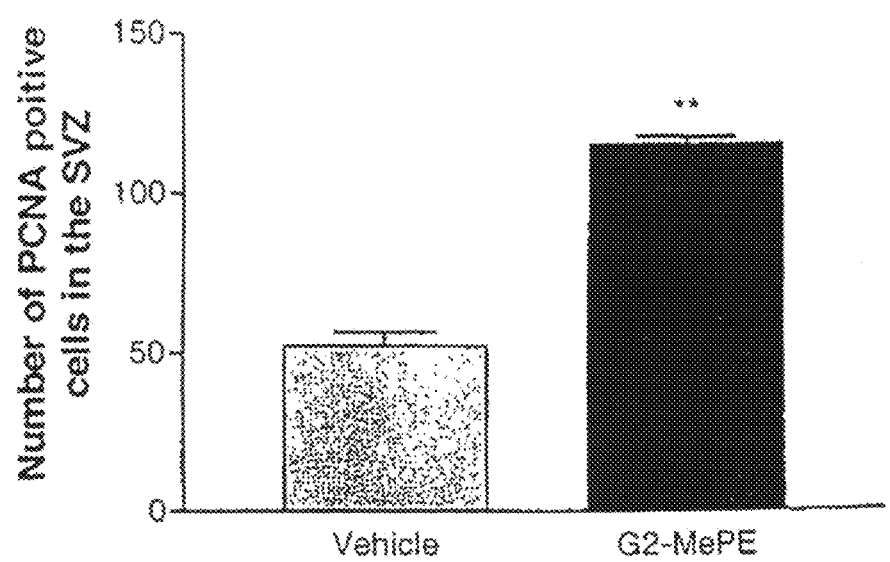
FIG. 19C shows effects of G-2MePE on neuroblast proliferation as assessed by PCNA immunohistochemical staining in middle-aged rats.

Fluorescence double labelling indicated co-localisation of PCNA with doublecortin, a marker for neuroblasts. FIG. 19B is a photograph of a portion of a rat's brain showing an increase in both PCNA (green, ×20) and doublecortin (red, ×20) in the rat treated with the highest dose of G-2MePE (right panel) compared to the vehicle treated rat (left panel). The two markers clearly co-localised (FIG. 19B, photo, ×100). We conclude that G-2MePE can stimulate proliferation of brain cells, including neuroblasts. Because neuroblasts are precursor cells for neurons, we further conclude that G-2MePE can increase the population of neurons in the brains of animals treated with the compound of this invention.
Experiment 2: G-2MePE Stimulates Neuroblast Proliferation in the SVZ of Brains of Middle-Aged Rats Effects of G-2MePE (1.2 mg/kg) were studied in a group of middle-aged, 9-month old rats. G-2MePE (1.2 mg/kg) or vehicle was administered intraperitoneally (i.p.). The proliferation of cells in the SVZ was examined 3 days after the treatment using PCNA immunohistochemical staining. FIG. 19C shows a significant increase in number of PCNA positive cells after the treatment of G-2MePE (**p<0.005, n=4). Because some of the proliferating cells stained with PCNA were identified as neuroblasts (see Experiment 1 above), we conclude that G-2MePE can stimulate neuroblast proliferation in middle-aged rat brains.
Experiment 3: Astrocytosis in Aging Brains Growing evidence suggests that dysfunction of astrocytes in advanced age can trigger inflammation, leading to further neuronal degeneration. Up-regulation of activated astrocytes has been well reported and is closely associated to memory decline with aging, perhaps through depressed endogenous neurogenesis.

Figure 20A:
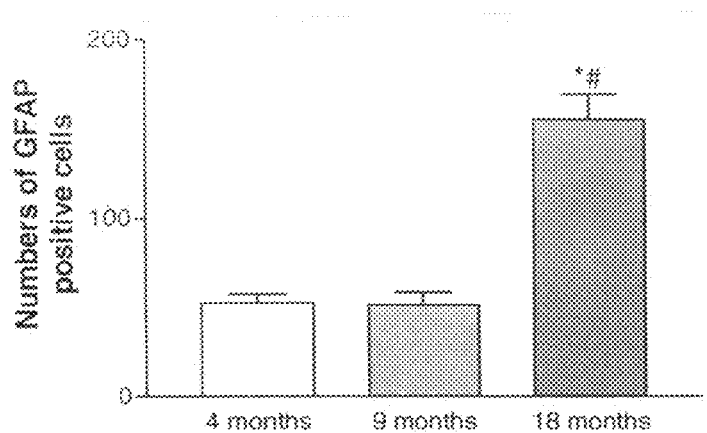
FIG. 20A shows a significant increase in the number of reactive astrocytes as assessed by GAPF staining in the hippocampus in aged rats compared to young rats (*$p<0.01$) and middle aged rats (*$p<0.01$).
Figure 20B:
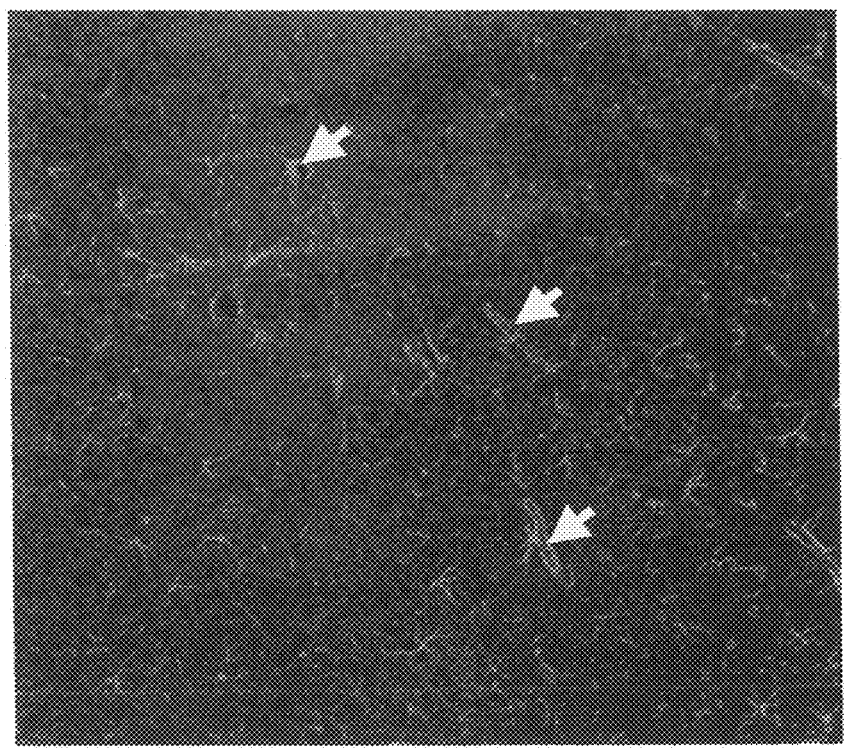
FIG. 20B shows a photograph of a section of cerebral cortex of an aged rat, showing astrocytes as assessed with GFAP staining, some of which are associated with formation of capillaries (arrows).

Using GFAP as a marker for reactive astrocytes, the number of GFAP-positive cells was counted in the CA4 subregion of the hippocampus of aged rats treated with G-2MeP or vehicle. We found a significant increase in reactive astrocytes in the hippocampus of aged animals (FIG. 20A), and in the cerebral cortex. Some of the astrocytes were associated with capillaries (FIG. 20B photo, arrows) in aged rats compared to both young (*p<0.01) and middle aged rats (*#p<0.01).

As part of the vascular component, GFAP positive astrocytes also plays a role in angiogenesis (FIG. 20B, arrows), which also contribute to inflammatory response in brains. Therefore the elevated GFAP astrocytes seen in aged brains may indicate a chronic stage of brain degeneration.
Experiment 4: G-2MePE Reduces Astrocytosis in Aged Brains We also evaluated effects of G-2MePE on astrocytosis in the CA4 sub-region of the hippocampus in aged rats. 18-month old male Wistar rats were assigned to 5 treatment groups as follows: vehicle, 0.12 mg/kg/day, 0.12, 1.2 and 12 mg/kg/day (each n=6).

Figure 20C:
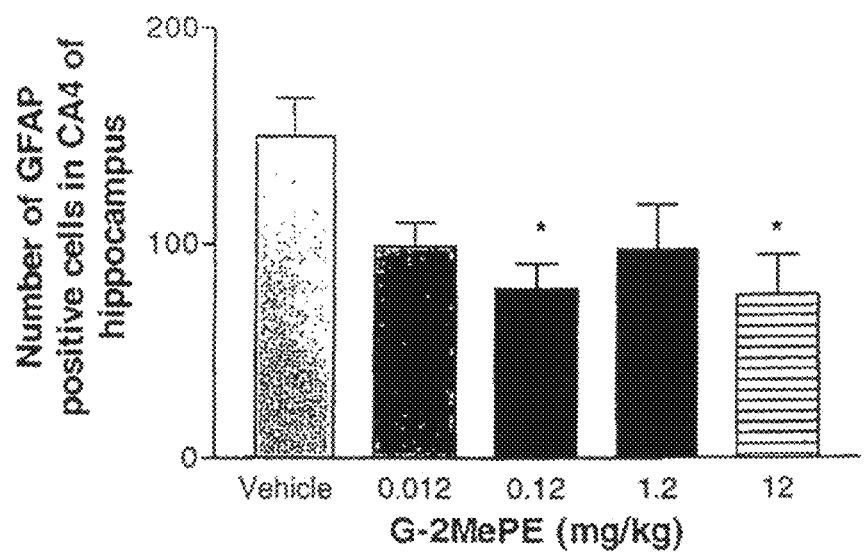
FIG. 20C shows dose-dependent effects of G-2MePE treatment (at doses of 0.12, 0.12, 1.2 and 12 mg/kg/day) on reduction of the number of astrocytes as assayed using GFAP staining in the CA4 sub-region of the hippocampus in aged rats.
Figure 20D:
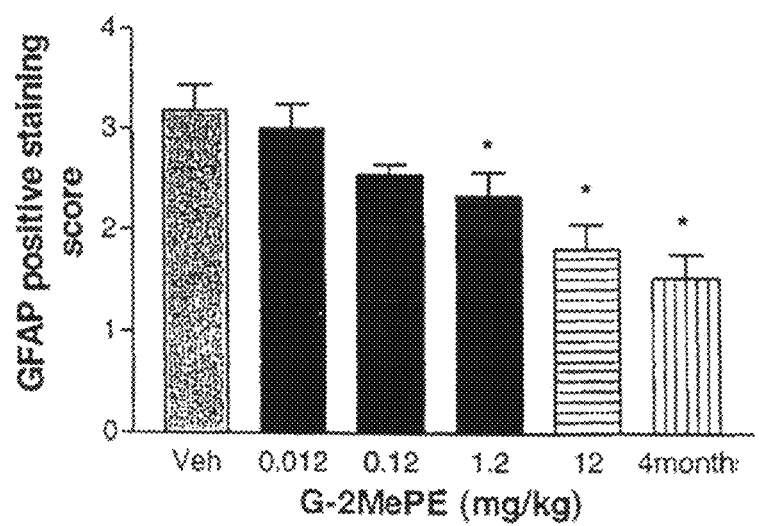
FIG. 20D shows dose-dependent effects of G-2MePE treatment (at doses of 0.12, 0.12, 1.2 and 12 mg/kg/day) on reduction of the number of astrocytes as assayed using GFAP staining in the cerebellar cortex.

GFAP-positive cells were counted using a computerised program (Discovery 1). Results are shown in FIGS. 20C and 20D. G-2MePE was administered intra-peritoneally and the numbers of GFAP-positive cells were assessed 3 d after the injection. Using a visual scoring system (0=no astrocytes, 1=few astrocytes, 0.2<50%, 3>50%) we estimated the number of astrocytes in 5 different cortical regions.

Treatment with G-2MePE reduced number of reactive astrocytes in the CA4 region of the hippocampus compared to the vehicle treated group (FIG. 20C; *p<0.05), particularly the groups treated with doses of 0.12 and 12 mg/kg. A similar effect was observed for G-2MePE in the cerebral cortex (FIG. 20D).

Normally there are few GFAP-positive astrocytes located in the deep layer of cortex of rat's brain; and those that are present are usually in close association with white matter tracks. However, we have found there were GFAP-positive cells in the middle layer of the cortex, closely associated with blood vessels.

Results of the studies presented herein indicate that aging is associated with several changes in the brain. First, there is an age-dependent loss of memory and cognitive function. Second, there is an age-depended increase in astrocytes. All of these findings in the rat are consistent with each other and the known roles of cholinergic nerves in maintaining cognitive function and memory in experimental animals and in humans.

We unexpectedly found that a GPE analog, G-2MePE, delivered to aged animals at least partially reverses all of the above age-associated changes. First, G-2MePE increases the amount of ChAT present in the brain cells of animals exposed to the neurotoxins okadaic acid or 3-NP. This effect of G-2MePE mimicked that of a well-known neuroprotective agent, GPE. These effects were seen in cortical cells, cerebellar cells and in striatal cells, indicating that the effects were widespread in different portions of the brain, Second, G-2MePE increased ChAT in the striatum, indicating that cholinergic neurons are sensitive to G-2MePE. These observed chemical and histological changes were paralleled by behavioural changes. Aged animals treated with G-2MePE exhibited improved memory in two well-known test systems compared to vehicle-treated controls. Next, G-2MePE induced neuroblast proliferation in aging brains. Finally, treatment with G-2MePE reversed the increase in astrocytosis observed in the hippocampus and cortex of aging brains. The effects of G-2MePE were not due to acute effects of the agent; because in many of the studies cited herein, sufficient time had elapsed from cessation of drug delivery to the test, that there was likely little or no drug present.

Example 7

Comparison of the Pharmacokinetics of GPE and G-2MePE

The purpose of these studies was to compare pharmacokinetic profiles of GPE and G-2MePE in animals in vivo using standard pharmacokinetic methods.
Methods Adult male Wistar rats weighing between 180 and 240 g were used to determine the pharmacokinetics of GPE and G2MePE. To facilitate intravenous bolus injections and blood sampling, all rats were surgically implanted with an indwelling jugular venous cannula under halothane anesthesia three days before the experiment. Groups of six rats were given a single intravenous bolus injection of either 30 mg/kg GPE or 10 mg/kg G2MePE dissolved in 0.1M succinate buffer (pH 6.5). Blood samples (about 220 µl each) were collected into heparinized tubes containing Sigma protease inhibitor cocktail for mammalian tissues at 10 and 0 min before injection of either GPE or G2MePE, and 1, 2, 4, 8, 16, 32, 64 and 128 min after injection of either GPE or G2MePE. The samples were centrifuged at 3000 g for 15 min at 4° C. and the plasma removed and stored at −80° C. until extraction and assay by either radioimmunoassay ("RIA") or reverse phase HPLC. The RIA and HPLC methods used were conventional.

Drug elimination after a single intravenous bolus injection was found to be a first-order process following the equation $C=C_0 e^{-kt}$, where C represents drug concentration in any time point, $C_0$ is the concentration when time (t) equals zero and k is the first-order rate constant expressed in units of concentration per hour. The k and half-life ($t_{1/2}$) were calculated from the slope of the linear regression line in the elimination phase of the semi-logarithmic plot of plasma concentration versus time as: Log $C=-kt/2.3+\log C_0$. Results were expressed as mean±standard error.

Results

Figure 21:
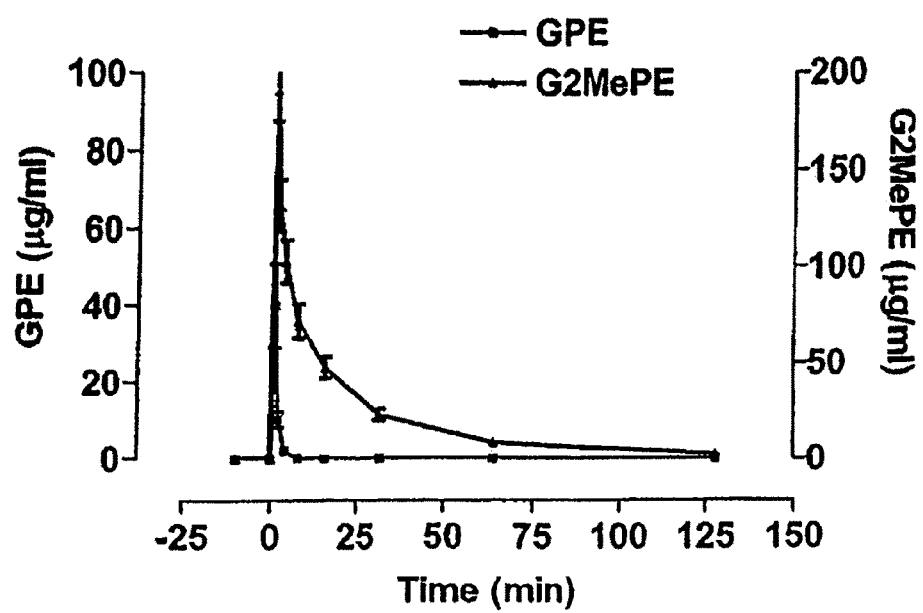
FIG. 21 shows pharmacokinetic properties of GPE and G-2MePE in the circulation of rats after intravenous injection.

FIG. 21 shows a graph of plasma concentrations in vivo of GPE and G-2MePE after intravenous (i.v.) injection. Filled squares represent concentrations of GPE at each time point, and filled triangles represent concentrations of G-2MePE at each time point.

Plasma concentrations of GPE and G-2MePE were markedly increased within 1 min after injection. After injection of 30 mg/kg GPE, a peak concentration of 40.0±10.8 mg/ml was observed. Plasma concentrations of GPE then rapidly declined according to a first-order kinetic process. The first order rate constant for GPE was found to be 0.15±0.014 ng/ml/min, the $t_{1/2}$ was found to be 4.95±0.43 min and the estimated clearance of GPE from plasma was found to be 137.5±12.3 ml/hr.

After injection of 10 mg/kg G-2MePE, the peak concentration was found to be 191±16.1 mg/ml. Plasma concentrations of G-2MePE then declined according to a first-order kinetic process. The first order rate constant for G-2MePE was found to be 0.033±0.001 ng/ml/min, the $t_{1/2}$ was found to be 20.7±0.35 min and the estimated clearance was found to be 30.1±0.5 ml/hr.

After injection, the maximal plasma concentration of G-2MePE was about 4.8 times greater than the maximal plasma concentration of GPE, in spite of the larger dose of GPE delivered (30 mg/kg) compared to the dose of G-2MePE delivered (10 mg/kg).

The finding of greater plasma concentrations of G-2MePE than for GPE at all time points less than 125 minutes, in spite of a lower delivered dose of G-2MePE was totally unexpected based on known plasma concentrations of GPE. The $t_{1/2}$ for G-2MePE was over 4 times longer than the $t_{1/2}$ for GPE.

The finding of increased half-life of G-2MePE compared to that of GPE was completely unexpected based on the $t_{1/2}$ of GPE. The increased $t_{1/2}$ of G-2MePE means that G-2MePE is cleared more slowly from the circulation. This finding is totally unexpected based on the clearance rate of GPE.

We conclude from these studies that G-2MePE is a potent agent capable of reversing many of the adverse effects of aging in the brains of animals, including humans. GPE analogs, including G-2MePE therefore, can produce desirable therapeutic effects, including neuroprotection, improved memory, increased neuroblast proliferation and reduction in astrocytosis, and can be valuable in reversing or mitigating adverse effects of aging in humans.

While this invention has been described in terms of certain preferred embodiments, it will be apparent to a person of ordinary skill in the art having regard to that knowledge and this disclosure that equivalents of the compound of this invention may be prepared and administered for the conditions described in this application, and all such equivalents are intended to be included within the claims of this application.

The invention claimed is:

1. A method for treating an animal having a condition characterized by a cognitive disorder or a memory disorder, comprising administering to that animal, directly or indirectly via the circulation, an effective amount of Glycyl-2-Methyl-L-Prolyl-L-Glutamate (G-2MePE) in the range of about 0.12 mg/kg to about 50 mg/kg, thereby increasing cognitive function.

2. The method of claim 1 where the condition is a memory loss or impairment associated with loss of neuronal cells.

3. The method of claim 2, wherein said neuronal cell loss is due to apoptosis, necrosis, or neuronal degeneration.

4. The method of claim 1 where the condition is a memory loss or mild cognitive disorder.

5. The method of claim 1 where the condition is a memory disorder or impairment due to aging or a neurodegenerative condition selected from the group consisting of Alzheimer's disease, Parkinson's disease, Huntington's disease and multiple sclerosis.

6. The method of claim 1 where the condition is a memory disorder due to hypoperfusion or hyperperfusion of the brain.

7. The method of claim 1 where the condition or memory loss is associated with type I diabetes or type II diabetes.

8. A method of enhancing cognitive function of an animal having a cognitive disorder due to aging, comprising administering the animal, either directly or indirectly via the circulation, an effective amount of G-2MePE.

9. The method of claim 1, wherein said condition can benefit from stimulation of neurogenesis in the brain of said animal.

10. The method of claim 1, wherein said condition can benefit from stimulation of production of neural cells containing choline acetyltransferase.

11. The method of claim 1, where said condition is characterized by astrocytosis.

12. The method of claim 1, wherein said G-2MePE is administered systemically, or parenterally.

13. The method of claim 1, wherein said G-2MePE is administered via an intravenous, subcutaneous, intranasal or oral route.

14. The method of claim 1, wherein said condition results from traumatic brain injury.

15. The method of claim 14, wherein said traumatic brain injury is a penetrating brain injury.

16. The method of claim 6, wherein said hypoperfusion is the result of stroke, cardiac artery bypass graft surgery (CABG), or myocardial infarction.

\* \* \* \* \*